(12) United States Patent
Georgiou et al.

(10) Patent No.: US 9,890,216 B2
(45) Date of Patent: Feb. 13, 2018

(54) ANTIBODIES WITH ENGINEERED IGG FC DOMAINS

(71) Applicant: THE BOARD OF REGENTS OF THE UNIVERSITY OF TEXAS SYSTEM, Austin, TX (US)

(72) Inventors: George Georgiou, Austin, TX (US); William Kelton, Austin, TX (US); Nishant Mehta, Basel (CH)

(73) Assignee: Board of Regents, The University of Texas System, Austin, TX (US)

( * ) Notice: Subject to any disclaimer, the term of this patent is extended or adjusted under 35 U.S.C. 154(b) by 59 days.

(21) Appl. No.: 14/437,544

(22) PCT Filed: Aug. 30, 2013

(86) PCT No.: PCT/US2013/057605
§ 371 (c)(1),
(2) Date: Apr. 22, 2015

(87) PCT Pub. No.: WO2014/065945
PCT Pub. Date: May 1, 2014

(65) Prior Publication Data
US 2015/0266960 A1   Sep. 24, 2015

Related U.S. Application Data

(60) Provisional application No. 61/717,568, filed on Oct. 23, 2012.

(51) Int. Cl.
| | | |
|---|---|---|
| *C07K 16/30* | (2006.01) | |
| *C07K 16/32* | (2006.01) | |
| *C07K 16/28* | (2006.01) | |
| *A61K 47/48* | (2006.01) | |
| *C07K 16/00* | (2006.01) | |
| *A61K 47/68* | (2017.01) | |

(52) U.S. Cl.
CPC .... *C07K 16/2863* (2013.01); *A61K 47/48561* (2013.01); *A61K 47/6849* (2017.08); *C07K 16/00* (2013.01); *C07K 16/30* (2013.01); *C07K 16/32* (2013.01); *C07K 2317/52* (2013.01); *C07K 2317/524* (2013.01); *C07K 2317/56* (2013.01); *C07K 2317/66* (2013.01); *C07K 2317/71* (2013.01); *C07K 2317/72* (2013.01); *C07K 2317/732* (2013.01); *C07K 2317/92* (2013.01)

(58) Field of Classification Search
CPC .... C07K 16/00; C07K 16/2863; C07K 16/30; C07K 16/32; C07K 2317/41; C07K 2317/52; C07K 2317/524; C07K 2317/56; C07K 2317/526; C07K 2317/71; C07K 2317/72; C07K 2317/732; C07K 2317/734; C07K 2317/92; C07K 2319/30; A61K 47/6801; A61K 47/6815; A61K 47/6813; A61K 47/6875; A61K 47/6879; A61K 47/6851; A61K 47/6849; A61K 51/10

See application file for complete search history.

(56) References Cited

U.S. PATENT DOCUMENTS

| 8,871,912 | B2 | 10/2014 | Davis | |
|---|---|---|---|---|
| 2005/0249723 | A1* | 11/2005 | Lazar | C07K 16/00 424/133.1 |
| 2010/0093979 | A1* | 4/2010 | Lazar | C07K 16/00 530/387.3 |
| 2011/0097323 | A1* | 4/2011 | Johnson | C07K 16/32 424/133.1 |
| 2012/0142593 | A1* | 6/2012 | Zhao | C07K 14/755 514/14.1 |
| 2012/0237506 | A1* | 9/2012 | Bossenmaier | C07K 16/00 424/133.1 |

FOREIGN PATENT DOCUMENTS

| WO | WO 1998/023646 | 6/1998 |
|---|---|---|
| WO | WO2010/111414 | * 9/2010 |

OTHER PUBLICATIONS

Yu et al., Investigative Ophthalmology & Visual Science 49(2): 522-527, Feb. 2008.*
Stancovski et al., PNAS, 88: 8691-8695, 1991.*
Herr et al., "Insights into IgA-mediated immune responses from the crystal structures of human FcαRI and its complex with IgA1-Fc", *Nature*, 423 (6940): 614-620, 2003, 2003.
International Preliminary Report on Patentability issued in International Application No. PCT/US2013/057605, dated May 7, 2015.
International Search Report and Written Opinion issued in International Application No. PCT/US2013/057605, dated Nov. 28, 2013.
Pleass et al., "Identification of residues in the CH2/CH3 domain interface of IgA essential for interaction with the human Fcα receptor (FcαR) CD89", *Journal of Biological Chemistry*, 274(33): 23508-23514, 1999.
Van Egmond et al., "Enhancement of Polymorphonuclear Cell-mediated Tumor Cell Killing on Simultaneous Engagement of FcγRI (CD64) and FcαRI (CD89)", *Cancer Research*, 61(10): 4055, 2001.
Woof et al., "Localisation of the monocyte-binding region on human immunoglobulin G", *Molecular Immunology*, 23(3): 319-330, 1986.
Woof et al., "Structure and function relationships in IgA", Mucosal Immunology, 4(6): 590-597, 2011.
Woof et al., "The human IgA-Fcα receptor interaction and its blockade by *Streptococcal* IgA-binding proteins", *Biochemical Society Transactions*, 30: 491-494, 2002.

* cited by examiner

*Primary Examiner* — Phuong Huynh
(74) *Attorney, Agent, or Firm* — Parker Highlander PLLC

(57) ABSTRACT

Antibody Fc polypeptides are provided that efficiently bind to both Fcγ and Fcα receptors. In certain aspects, a Fc polypeptide comprises a chimeric IgG CH2 domain having a α1 loop from IgA and an IgA CH3 domain. Recombinant antibodies comprising Fc polypeptides of the embodiments and methods for making and using such antibodies are likewise provided.

20 Claims, 16 Drawing Sheets

US 9,890,216 B2

ANTIBODIES WITH ENGINEERED IGG FC DOMAINS

This application is a national phase application under 35 U.S.C. §371 of International Application No. PCT/US2013/057605, filed Aug. 30, 2013, which claims the benefit of U.S. Provisional Patent Application No. 61/717,568, filed Oct. 23, 2012, the entirety of each of which is incorporated herein by reference.

INCORPORATION OF SEQUENCE LISTING

The sequence listing that is contained in the file named "UTFB_P1003WO_ST25.txt", which is 53 KB (as measured in Microsoft Windows®) and was created on Aug. 22, 2013, is filed herewith by electronic submission and is incorporated by reference herein.

BACKGROUND OF THE INVENTION

1. Field of the Invention

The present invention relates generally to the field of molecular biology and immunology. More particularly, it concerns molecular antibody design and antibody-based reagents and therapeutics.

2. Description of Related Art

Antibody therapeutics have a dominant market share in the treatment of cancers and other human diseases with estimated sales exceeding USD $56 billion in 2011. Antibodies kill cancer cells in part by engaging and activating immune cells. One important mechanism underlying the potency of antibody therapeutics is the ability of antibody to recruit immune cells to a target antigen (or cell). Thus, the Fc region of an antibody is crucial for recruitment of immunological cells and antibody dependent cytotoxicity (ADCC). In particular, the nature of the ADCC response elicited by antibodies depends on the interaction of the Fc region with receptors (FcRs) located on the surface of many cell types. Humans contain five different classes of Fc receptors. In addition haplotypes, or genetic variants of different FcRs belonging to a particular class are known. The binding of an antibody to FcRs determines its ability to recruit other immunological cells and the type of cell recruited. Hence, the ability to engineer antibodies that can recruit only certain kinds of cells can be critically important for therapy.

Currently, all antibody therapeutics are of the IgG subclass. Therapeutic IgG antibodies engage the Fcγ class of receptors via Fc domain interaction on the surface of various blood cells which in turn become activated to kill tumor cells. For some therapeutics efficacy could be improved by the additional recruitment of cells that display Fcα or Fcα receptors. However, to date, antibody Fc polypeptides have not been identified that can bind to additional Fc receptors.

SUMMARY OF THE INVENTION

In a first embodiment there is provided a chimeric polypeptide comprising a CH2 and CH3 domain of a mammalian immunoglobulin molecules, wherein the polypeptide binds to at least one Fcα receptor and at least one Fcγ receptor. For example, in certain aspects, a chimeric polypeptide binds to a FcγRI or FcγRIIa with a higher affinity than an IgA antibody. In further aspect, a chimeric polypeptide binds to FcαRI with a higher affinity than an IgG antibody. In still a further aspect, a chimeric polypeptide binds to a FcγRIIb with a lower affinity than an IgG antibody.

In a further embodiment, a chimeric polypeptide is provided comprising (a) a chimeric CH2 domain comprising a mammalian IgG Fc CH2 domain having a α1 and/or α2 loop of a mammalian IgA Fc CH2 domain; and (b) a mammalian IgA Fc CH3 domain. In some aspects, the mammalian IgA Fc CH3 domain is defined as a mammalian IgA Fc CH3 domain corresponding to amino acids 336-443 of a human IgA Fc, such as a human IgA1 (SEQ ID NO:9) or IgA2 CH3 domain, based on the Kabat numbering scheme. IgA CH3 domains from several exemplary mammalian species are depicted in the alignment shown in FIG. 19. In certain aspects, the α1 loop of a mammalian IgA is defined as a mammalian IgA α1 loop corresponding to amino acids 245-257 of a human IgA Fc, according to the Kabat numbering scheme (e.g., a human IgA1 or IgA2 α1 loop). IgA α1 loop domains from several exemplary mammalian species are depicted in the alignment shown in FIG. 19. Thus, in some aspects, the α1 loop of a mammalian IgA Fc CH2 domain comprises the sequence PALEDLLLGSEAN (SEQ ID NO: 14) or PALEDLLLGSEANG (SEQ ID NO: 15) (which includes an additional such that the length of the sequence corresponds with that of the IgG1 loop sequence). In yet a further aspect, a chimeric polypeptide is provided comprising (a) a chimeric CH2 domain comprising a mammalian IgG Fc CH2 domain having a α1 loop of a mammalian IgA Fc CH2 domain; and one, two or three amino acid positions from the α2 loop of a mammalian IgA Fc CH2 domain; and (b) a mammalian IgA Fc CH3 domain. Thus, in certain aspects, a chimeric polypeptide of the embodiments comprises an amino acid sequence at least 85%, 90%, 91%, 92%, 93%, 94%, 95%, 96%, 97%, 98% or 99% identical to SEQ ID NO: 7 or SEQ ID NO: 8. For example, the chimeric polypeptide can comprise a sequence identical to SEQ ID NOs: 3, 4, 7 or 8.

In further aspects, a chimeric antibody of the embodiments further comprises a FcRn-binding peptide, such as FcRn-binding peptide positioned at the c-terminus of the chimeric antibody. For example, the FcRn-binding peptide can comprise the linear peptide of SEQ ID NO: 67 or the cyclic peptide of SEQ ID NO: 68.

In still a further embodiment there is provided a chimeric polypeptide of the embodiments comprises an amino acid sequence at least 85%, 90%, 91%, 92%, 93%, 94%, 95%, 96%, 97%, 98% or 99% identical to SEQ ID NO: 7 or SEQ ID NO: 8. For instance, the chimeric polypeptide can comprise a sequence identical to SEQ ID NOs: 3, 4, 7 or 8.

In a further embodiment there is provided a polynucleotide molecule encoding a chimeric polypeptide of the embodiments. In certain aspects the polynucleotide further encodes a promoter, enhancer, polyadenylation sequence, intron, drug selection marker, origin of replication, a reporter or a purification tag. For example, the isolated polynucleotide can be comprised in a polynucleotide expression vector.

In a further aspect, a chimeric polypeptide further comprises a mammalian IgG Fc CH1 domain, an IgG VH domain and/or a hinge domain. Thus, in some aspects, a recombinant antibody is provided comprising a chimeric polypeptide of the embodiments. For example, the recombinant antibody can be a human or humanized antibody. In yet further aspects, the chimeric antibody is an aglycosylated antibody.

In certain aspects, an antibody of the embodiments binds to a cell surface antigen or to a cancer cell antigen. For example, in certain aspects, an antibody binds to an EGFR (e.g., HER1 or HER2) or VEGFR. In certain aspects, an antibody of the embodiments bind to the same antigen as one of the antibodies selected from Table A. In still a further aspect, an antibody of the embodiments comprise CDRs 1, 2, 3, 4, 5 and 6 of an antibody of Table A.

In further aspects an antibody according to the embodiments is coupled to a therapeutic, a reporter, or a targeting moiety. For example, the therapeutic can be a polynucleotide (e.g., a miRNA, a siRNA or an therapeutic gene), a peptide, a small molecule, a therapeutic radionuclide, a chemotherapeutic, a tumor suppressor, an apoptosis inducer, an enzyme, a second antibody, an siRNA, a hormone, a prodrug, or an immunostimulant. Examples of reporters include, but are not limited to, radionuclides, florophores, MRI contrast agents, enzymes, dyes or molecules detectable by positron emission tomography (PET).

In yet further aspects, an antibody of the embodiments comprises one or more of the following: (a) decreased affinity for FcγRIIb relative to a wild type IgG1 antibody; (b) increased affinity for FcγRIIa relative to a wild type IgA1 antibody; (c) increased affinity for FcγRI relative to a wild type IgA1 antibody; and/or (d) increased affinity for FcαRI relative to a wild type IgG1 antibody.

In some embodiments, the invention provides a pharmaceutical composition comprising a chimeric polypeptide or a recombinant antibody of the embodiments in a pharmaceutically acceptable carrier.

In a further embodiment there is provided a method of making a polypeptide comprising: (a) expressing a recombinant polynucleotide encoding a chimeric polypeptide of the embodiments in a cell; and (b) obtaining a polypeptide expressed by the cell. For example, the cell can be a bacterial cell, a yeast cell, a ciliate cell, or an insect cell.

In still a further embodiment, there is provided a method treating a subject comprising administering an effective amount of an antibody of the embodiment to the subject. In certain aspects, the subject has an autoimmune disease or a cancer. For example, in some aspects, the subject has one of the diseases indicated in Table A. Routes for administering an antibody include, without limitation, by intravenous administration, intracardiac administration, intradermal administration, intralesional administration, intrathecal administration, intracranial administration, intrapericardial administration, intraumbilical administration, intraocular administration, intraarterial administration, intraperitoneal administration, intraosseous administration, intrahemmorhage administration, intratrauma administration, intratumor administration, subcutaneous administration, intramuscular administration, intravitreous administration, direct injection into a normal tissue, or by direct injection into a tumor.

In certain embodiments, there is provided an isolated or recombinant HER2-binding antibody wherein the antibody comprises a chimeric immunoglobulin heavy constant region of the embodiments. In some aspects, a HER2-binding antibody of the embodiments comprises 1, 2, 3, 4, 5, or all 6 of the CDRs of the Trastuzumab monoclonal antibody. For example, the HER2-binding antibody can comprises an amino acid sequence at least about 75%, 80%, 85%, 90%, 95%, 98% or 99% identical to the heavy chain and/or light chain variable region amino acid sequence of the Trastuzumab monoclonal antibody.

In certain embodiments, there is provided an isolated or recombinant HER1-binding antibody wherein the antibody comprises a chimeric immunoglobulin heavy constant region of the embodiments. In some aspects, a HER1-binding antibody of the embodiments comprises 1, 2, 3, 4, 5, or all 6 of the CDRs of the Cetuximab monoclonal antibody. For example, the HER1-binding antibody can comprises an amino acid sequence at least about 75%, 80%, 85%, 90%, 95%, 98% or 99% identical to the heavy chain and/or light chain variable region amino acid sequence of the Cetuximab monoclonal antibody.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1B: Wild-type IgA sequence with alanine scanning mutations underlined (SEQ ID NO: 13).

DESCRIPTION OF ILLUSTRATIVE EMBODIMENTS

I. The Present Invention

Antibody-based therapeutics have recently been approved for treatment of a wide range of diseases from cancer to autoimmune disease (see, e.g., Table A). Recently, recombinant antibodies have even been developed for treatment of infectious disease. However, the efficacy of most antibody-based therapeutics is dependent on the effector function of cells and factors that bind to the antibodies, such as complement. For example, antibodies that target specific cell types are currently used as anticancer therapies, but many antibodies are either not directly toxic to the cancer cells or have low cytotoxicity. Thus, despite the targeting specificity of such antibodies, many fail to exhibit sufficient effect (e.g., cell killing) on target cells.

In contrast to IgG, which have been the only type of therapeutic antibody used to date, antibodies that belong to the IgA class engage the widely expressed FcαRI receptor on neutrophils. These cells comprise the greatest fraction of innate effector cells found in circulation and can activate potent inflammatory action when FcαRI is cross-linked by IgA immune complexes. Both antibody dependent cell mediated cytotoxicity (ADCC) (oxidative burst, degranulation) and antibody dependent cell mediated phagocytosis (ADCP) responses have been observed upon FcαRI activation. However, IgG antibodies do not engage the FcαRI receptor and hence poorly activate neutrophils and other granulocytes.

Despite their potential promise, use of the IgA antibody isotype to exploit the potent inflammatory effects of FcαRI in a therapeutic setting has so far been disfavored due to low expression yields and expensive purification schemes required for IgA antibodies. Further, IgA antibodies do not display the favorable therapeutic functions that IgG antibodies do. Combination therapy of IgA with IgG is likewise undesirable both due to regulatory and cost concerns and also due to the blocking of neutrophils activated via FcαRI action by the engagement of the FcγRIIb receptor by IgG.

Figure 3:
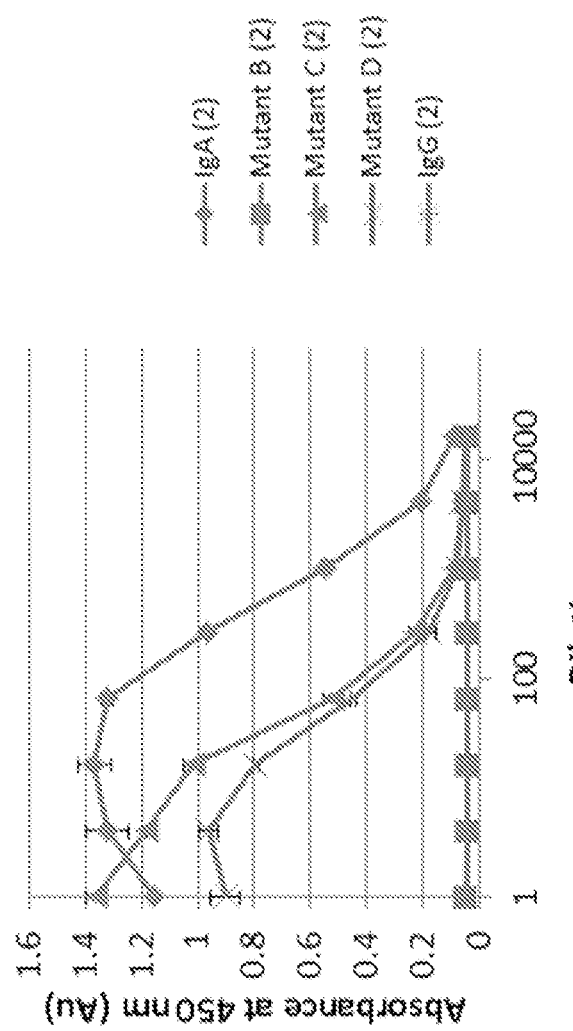
FIG. 3: Graph shows the binding of chimeric Fc polypeptides of the embodiments to FcαRI-GST as assessed by ELISA assay.
Figure 4:
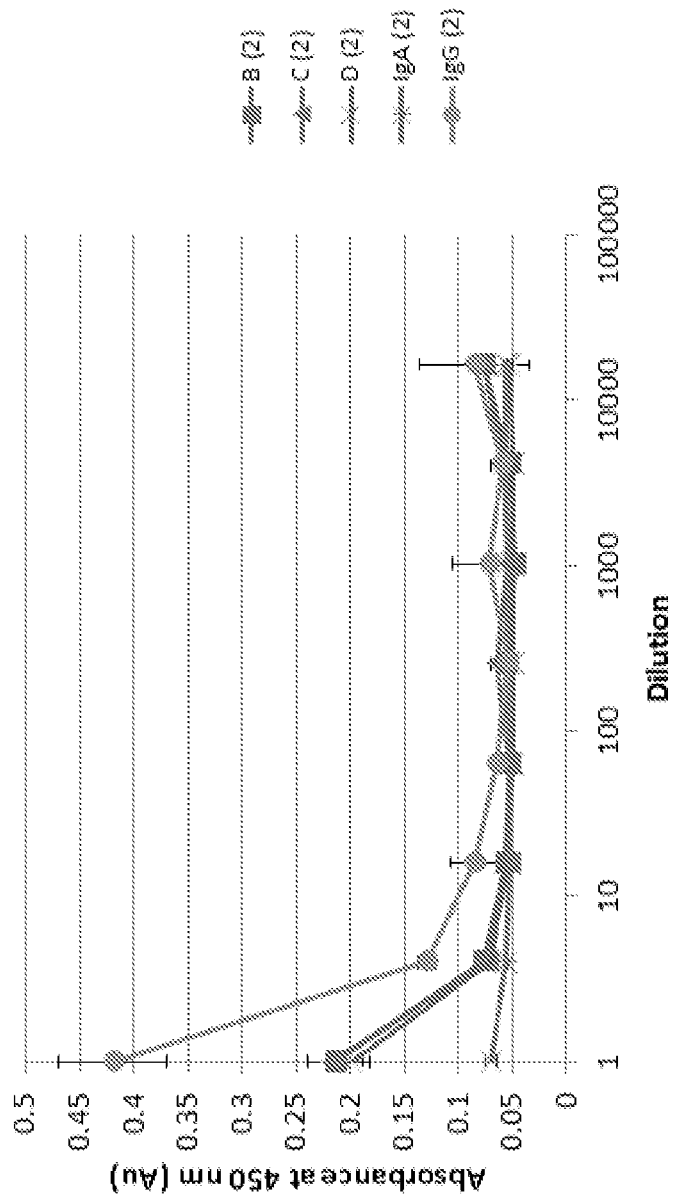
FIG. 4: Graph shows the binding of chimeric Fc polypeptides of the embodiments to FcγRI as assessed by ELISA assay.
Figure 5:
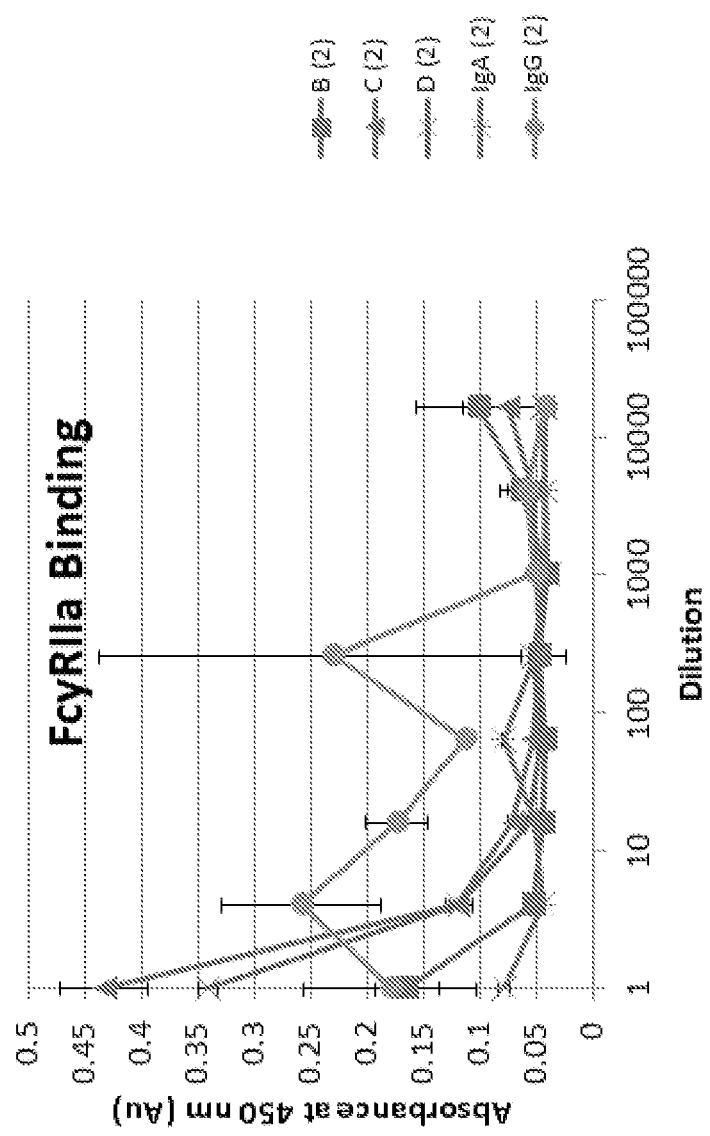
FIG. 5: Graph shows the binding of chimeric Fc polypeptides of the embodiments to FcγRIIa as assessed by ELISA assay.
Figure 6:
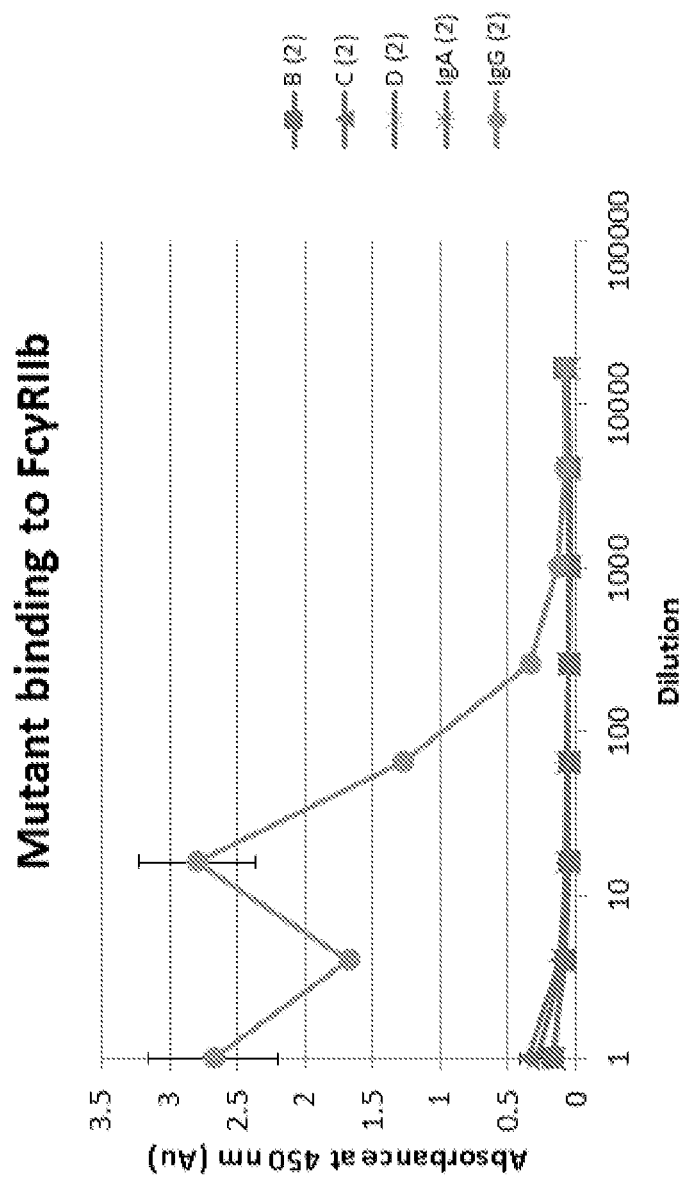
FIG. 6: Graph shows the binding of chimeric Fc polypeptides of the embodiments to FcγRIIb as assessed by ELISA assay.

The polypeptides and antibodies provided herein address these issues by providing Fc domains that are able to bind both Fcα and Fcγ receptors. Specifically, an IgG1 antibody Fc domain has been engineered to introduce de novo binding to the IgA FcαRI receptor while retaining existing affinity for FcγRs. For example, chimeric Fc domains that comprise sequences from both IgG and IgA Fc's are shown to have significant FcαRI binding (see FIG. 3). Nonetheless, the polypeptides retain significant binding to FcγRI and FcγRIIa (FIGS. 4-5). Perhaps most importantly, the new chimeric Fc polypeptides retain only limited affinity for FcγRIIb, a receptor that can block activation of key effect cells such as neutrophils (FIG. 6). Moreover, chimeric antibodies could be further modified by the additional of an FcRn binding peptide (FIG. 18), a modification that may increase serum half life of the molecules. Thus, the new chimeric Fc polypeptides and antibodies that incorporate the polypeptides offer a broader range of effector function relative to either IgG or IgA alone, which could greatly improve the efficacy of new antibody therapeutics. Moreover, the new chimeric Fc polypeptides can be used to replace the Fc domains of existing antibody therapeutics, thereby rendering them more effective. This effect is exemplified in studies presented here. For example, when a chimeric Fc domain (MutD) was fused to trastuzumab the new chimeric antibody was able to mediate neutrophil killing of Her expressing cells with high efficiency (see FIG. 17).

II. IgA and FcαRI

Monomeric IgA is the second most abundant immunoglobulin in human serum after the IgG isotype. IgA antibodies, typically implicated in mucosal surface defense, are represented in higher serum concentrations in humans than in the sera of other animal species. Together, the two IgA allotypes comprise up to 25% of human serum immunoglobulins. Also unique to humans is the high proportion of monomeric serum IgA (~90%) as opposed to J chain linked dimeric forms (Woof and Kerr, 2006).

IgA binds selectively to the FcαR1 (CD89) receptor, which is constitutively expressed on cells of the myeloid lineage, including neutrophils, macrophages, and eosinophils, in humans. Membrane anchored FcαRI is found expressed with or without association to the Fcγ signaling chain. If unassociated, FcαRI internalizes and recycles IgA to the cell surface. However, even with this recycling mechanism, the circulation half-life is significantly less than that of IgG at 5.9 days for serum IgA1 and 4.5 days for serum IgA2 (Morell et al., 1973). On the other hand, association of IgA chains with CD89 is essential for IgA facilitated Ag presentation, oxidative burst, cytokine release, and tumor killing (Jacob et al., 2008). There are at least ten spliced isoforms of CD89 reported, the majority of which have undefined functions (Qian et al., 2008). Despite significant effort, a murine homologue of this receptor has not been identified. It has been suggested that mice lost the FcαR1 gene during a translocation event from chromosome 7 to the X chromosome (Woof and Kerr, 2004). IgA immune complexes have been reported to induce strong inflammatory responses and demonstrate efficient tumor killing by neutrophil recruitment upon binding FcαRI (van Egmond et al., 2001; Stockmeyer et al., 2000). In fact, tumor killing by IgA activation of the FcαR1 receptor on neutrophils has been shown to be more potent than IgG tumor killing by activation of FcγR1 and co-activation of both receptors by bispecific antibodies showed an additive effect in tumor treatment. However, therapeutic dosing with full-length IgA and IgG in combination was less successful as the Fc domain of IgG1 binds FcγRIIb, an inhibitory receptor, which reduced the tumor killing efficiency of IgA. Development of an IgA Fc domain engineered to bind the FcγR1 receptor has the potential to exploit both tumor killing pathways without activation of inhibitory functions.

IgA antibodies have not yet received attention for therapeutic applications partially because their production is costly and inefficient but also because their half-life in serum is shorter than that of IgG antibodies. Part of the concern in IgA expression is the heavily glycosylated hinge region that includes up to five O-linked glycosylation sites. Glycosylation not only impacts the expression level but also introduces the potential for large glycan heterogeneity during production. By engineering FcαRI binding into an IgG molecule, many of these concerns can be alleviated. To further define the FcαRI binding pocket in IgA1, point mutations were generated in either of two interdomain loops (Leu-257-Gly-259 in the CH2 domain; Pro-440-Phe-443 in the CH3 domain). Each substitution, with the exception of G259R, resulted in greatly ablated FcαRI binding.

II. Modified Proteins and Polypeptides

Embodiments concerns modified polypeptides, in particular polypeptides comprising chimeric Fc domains that confer binding to both IgGγ and IgGa receptors. Preferably the chimeric polypeptides have limited binding affinity for IgGγIIb. Polypeptides of the embodiments comprise portions of an IgG Fc domain (e.g., an IgG1 Fc) and portions of an IgA Fc domain. In certain aspects, a chimeric polypeptide comprises a Fc CH2 and CH3 domain sequence that is composed of chimeric domains of human IgA (e.g., IgA1 or IgA2, NCBI accession nos. P01876.2 and P01877.3, respectively incorporated herein by reference; see also SEQ ID NO: 9) and human IgG (e.g., IgG1, IgG2, IgG3 or IgG4, NCBI accession nos. P01857.1; P01859.2; P01860.2; and P01861.1, respectively, incorporated herein by reference). As used herein, numbering of amino acid position in a chimeric polypeptide refers to the standard nomenclature set forth, e.g., in Kabat et al., 1991, incorporated herein by reference.

CH3 Domain

In certain aspects, a chimeric polypeptide of the embodiments comprises a CH3 from a mammalian immunoglobulin. Preferably the CH3 is substantially homologous to a human IgA CH3 domain. For example, the CH3 domain can be at least about 85%, 90%, 91%, 92%, 93%, 94%, 95%, 96%, 97%, 98%, 99% or 100% identical to the CH3 of a human IgA1 or IgA2 (see, e.g., NCBI accession nos. P01876.2 and P01877.3, incorporated herein by reference). In further aspects, a CH3 domain of the embodiment may comprise 1, 2, 3, 4, 5, 6, 7, 8, 9 or 10 amino acid positions that are substituted with the amino at a corresponding position of an IgG CH3 domain, such as a human IgG1. Thus, in certain specific aspects, a chimeric polypeptide of the embodiments comprises a CH3 domain that is 85%, 90%, 91%, 92%, 93%, 94%, 95%, 96%, 97%, 98%, 99% or 100% identical to a CH3 domain (positions 336-443; SEQ ID NO: 9) of a human IgA1.

Figure 1A:
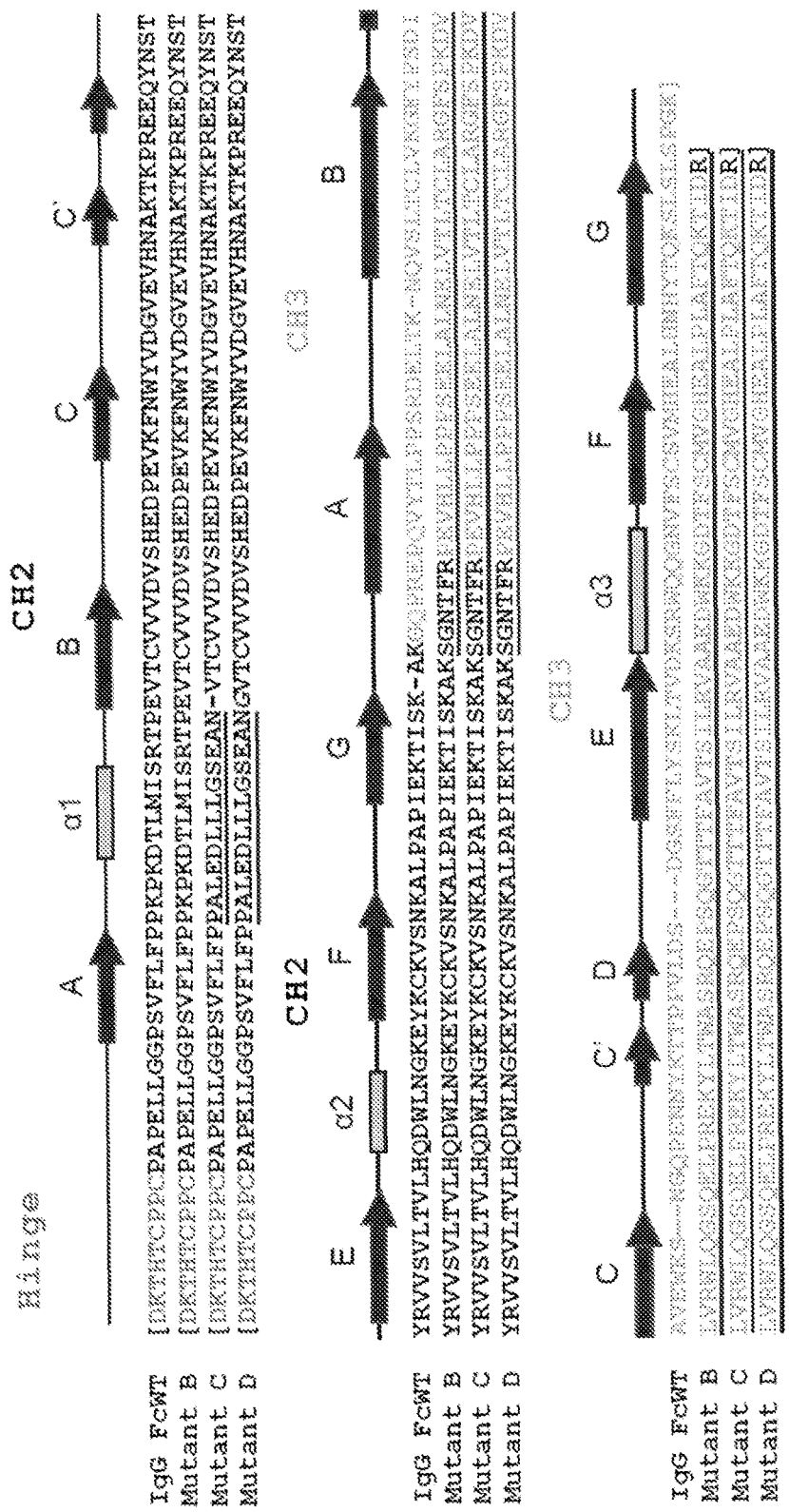
FIG. 1A-B—FIG. 1A: Amino acid alignment of mutants B (SEQ ID NO: 2), C (SEQ ID NO: 3), and D (SEQ ID NO: 4) with wild-type IgG1 (SEQ ID NO: 1). Black lettering is CH2 sequence; gray lettering is CH3 sequence; underlined lettering is derived from IgA1. The additional glycine in mutant D is italicized.
Figure 1B:
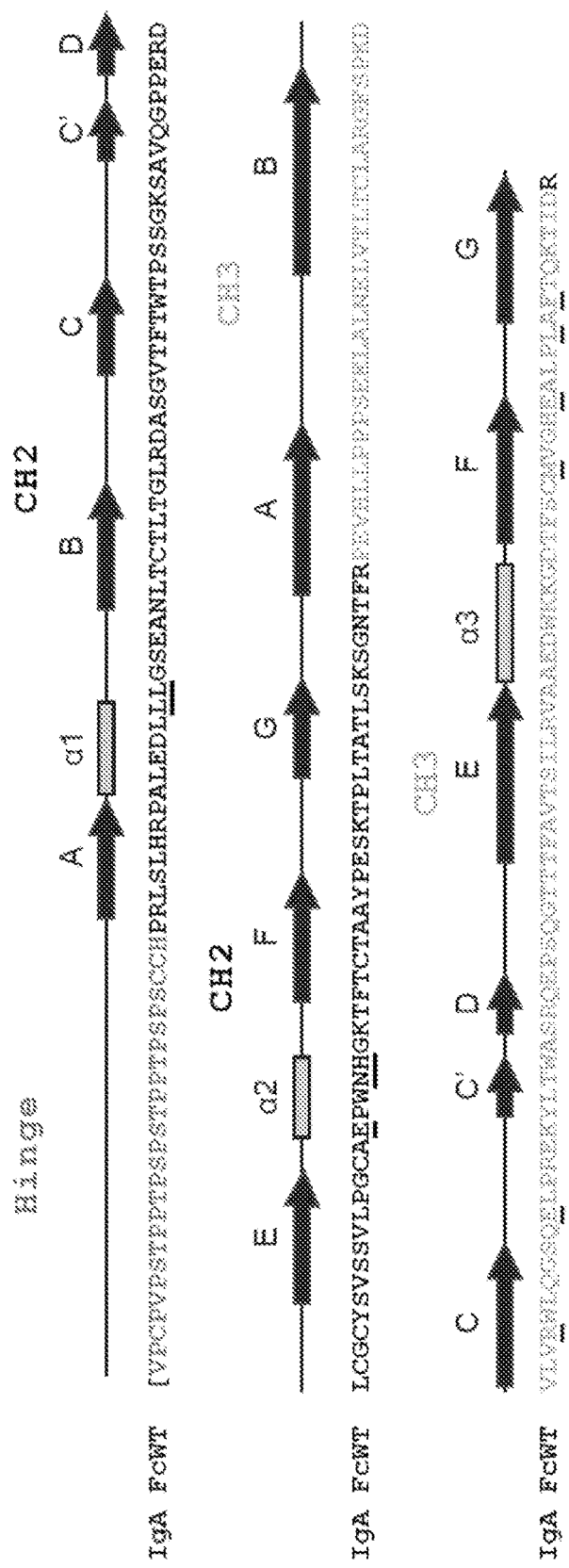

In still further aspects, a chimeric polypeptide of the embodiments comprises a CH3 domain that is 85%, 90%, 91%, 92%, 93%, 94% or 95%, identical to a CH3 domain (positions 336-443; SEQ ID NO: 10) of a human IgG1 and comprising 1, 2, 3, 4, 5, 6, 7, 8, 9 or 10 amino acid positions that are substituted with the amino at a corresponding position of an IgA CH3 domain, such as a human IgA1. For example, the CH3 domain of a chimeric polypeptide can comprise an amino acid substitution corresponding to F443, E437, M433, E389 and/or R382, as shown in FIG. 1B.

CH2 Domain

A chimeric polypeptide of the embodiments, in certain aspects, comprises a chimeric CH2 from a mammalian immunoglobulin. Preferably, the chimeric CH2 domain comprises chimeric domains of human IgG and IgA CH2 domains. For example, the CH2 domain can comprise a IgG CH2 domain having an α1 and/or α2 loop domain from an IgA. In some specific aspects, a chimeric CH2 domain comprises a CH2 domain from a human IgG1 having an α1 and/or α2 loop domain from a human IgA1. In still further aspects a chimeric CH2 domain comprises a CH2 domain from a human IgG1 having 1, 2, 3, 4 or 5 amino acids substituted for an amino acid at a corresponding position in an α1 and/or α2 loop domain from a human IgA1. Thus, in some aspects, a chimeric CH2 domain of the embodiments is at least about 85%, 90%, 91%, 92%, 93%, 94%, 95%, 96%, 97%, 98%, 99% or 100% identical to the CH2 of the "Mutant C" or "Mutant D" polypeptide (SEQ ID NOs:11 and 12, respectively). In still further aspects, a CH2 domain of the embodiment may comprise 1, 2, 3, 4, 5, 6, 7, 8, 9 or 10 amino acid positions that is a substituted with the amino at a corresponding position of an IgA CH2 domain, such as a human IgA1. For example, the CH2 domain of a chimeric polypeptide can comprise an amino acid substitution corresponding to N316, E313 and/or L258, as shown in FIG. 1B.

In some aspects, a chimeric CH2 domain of the embodiments can comprise a conservative amino acid insertion, deletion of substitution as further outlined below. For instance the chimeric CH2 domain can comprise an amino acid insertion to maintain the relative lengths of domains between IgG and IgA, as was done in the case of the "Mutant D" polypeptide where a Gly was inserted after the IgA α1 loop sequence.

Additional Domains

In certain aspects, a chimeric polypeptide of the embodiments further comprises a CH1 and/or hinge domain from a mammalian immunoglobulin. Preferably the CH1 and/or hinge domain are from a human IgG polypeptide. For example, the CH1 and/or hinge domain can be a at least about 85%, 90%, 91%, 92%, 93%, 94%, 95%, 96%, 97%, 98%, 99% or 100% identical to the CH1 and/or hinge domain of a human IgG1, IgG2, IgG3 or IgG4 (see, e.g., NCBI accession nos. P01857.1; P01859.2; P01860.2; and P01861.1, incorporated herein by reference). In some aspects, a CH1 domain of the embodiments can comprise a conservative amino acid insertion, deletion of substitution as outlined below.

In still further aspects a chimeric polypeptide of the embodiments further comprises a VH domain. In further aspects, a chimeric polypeptide is further associated with (e.g., via disulfides bonds) an immunoglobulin light chain.

Thus, in some aspects, a chimeric polypeptide of the embodiments comprises an antibody.

It is further contemplated that additional modifications could be made to a chimeric polypeptide of the embodiments. For example, a modified chimeric polypeptide can be made that exhibits at least one functional activity that is comparable to the unmodified version, yet the modified protein or polypeptide possesses an additional advantage over the unmodified version, such as cheaper to production, eliciting fewer side effects, and/or having better or longer efficacy or bioavailability. Thus, when the present application refers to the function or activity of a "modified chimeric polypeptide" one of ordinary skill in the art would understand that this includes, for example, polypeptide that 1) performs at least one of the same activities or has at least one of the same specificities as the unmodified polypeptide, but that may have a different level of another activity or specificity; and 2) possesses an additional advantage over the unmodified polypeptide. Determination of activity may be achieved using assays familiar to those of skill in the art, particularly with respect to the protein's activity, and may include for comparison purposes, for example, the use of native and/or recombinant versions of either the modified or unmodified protein or polypeptide. In addition to the modified polypeptides discussed herein, embodiments may involve domains, polypeptides, described in WO 2008/137475, which is hereby specifically incorporated by reference.

Modified chimeric polypeptides may possess deletions and/or substitutions of amino acids; thus, a protein with a deletion, a protein with a substitution, and a protein with a deletion and a substitution are modified proteins. In some embodiments these modified proteins may further include insertions or added amino acids, such as with fusion proteins or proteins with linkers, for example (see, e.g., the Gly insertion in "Mutant D" polypeptide). A "modified deleted polypeptide" lacks one or more residues of the native protein, but possesses the specificity and/or activity of the native polypeptide. A "modified deleted polypeptide" may also have reduced immunogenicity or antigenicity. An example of a modified deleted polypeptide is one that has an amino acid residue deleted from at least one antigenic region—that is, a region of the protein determined to be antigenic in a particular organism, such as the type of organism that may be administered the modified protein.

Substitutional or replacement variants typically contain the exchange of one amino acid for another at one or more sites within the polypeptide and may be designed to modulate one or more properties of the polypeptide, particularly its effector functions and/or bioavailability. Certain specific amino acid exchanges in chimeric polypeptides of the embodiments are detailed above. Further substitutions may or may not be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

In addition to a deletion or substitution, a modified polypeptide may possess an insertion of residues, which typically involves the addition of at least one residue in the polypeptide. This may include the insertion of a targeting polypeptide or simply a single residue. Terminal additions, called fusion proteins, are discussed below.

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes. Thus, in certain, aspects a chimeric polypeptide of the embodiments comprises from N- to C-terminus: a VH domain-CH1 domain-hinge domain-chimeric CH2 domain-a CH3 domain (e.g., an IgA CH3 domain).

The following is a discussion on strategies for changing of the amino acids of a polypeptide to create an equivalent, or even an improved, second-generation molecule. For example, certain amino acids may be substituted for other amino acids in a polypeptide structure with or without appreciable loss of interactive binding capacity with structures such as, for example, binding sites to substrate molecules. This is especially possible in polypeptides that have a well know structure, such as antibody polypeptides (see, e.g., in Kabat et al., 1991).

In making changes, in some cases, the hydropathic index of amino acids may be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still produce a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

III. Nucleic Acid-Based Expression Systems

Nucleic acid-based expression systems may find use, in certain embodiments of the invention, for the expression of recombinant polypeptides and antibodies of the embodiments. Thus, certain aspects of the embodiments concern polynucleotide that encode a chimeric polypeptide of the embodiments. Below is a discussion of polynucleotide vector for expression of chimeric polypeptides and methods for production of the polypeptides. As used herein the terms "polynucleotide" and "nucleic acids" are used interchangeably.

A. Methods of Polynucleotide Delivery

Certain aspects of the embodiments may comprise delivery of polynucleotide to target cells (e.g., host cells). For example, bacterial, yeast or mammalian host cells may be transformed with nucleic acids encoding chimeric polypeptides. Suitable methods for nucleic acid delivery for transformation of a cell are believed to include virtually any method by which a nucleic acid (e.g., DNA) can be introduced into such a cell, or even an organelle thereof. Such methods include, but are not limited to, direct delivery of DNA such as by injection (U.S. Pat. Nos. 5,994,624, 5,981, 274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783; 5,563,055; 5,550,318; 5,538,877 and 5,538,880, and each incorporated herein by reference); or by agitation with silicon carbide fibers (Kaeppler et al., 1990; U.S. Pat. Nos. 5,302,523 and 5,464,765, each incorporated herein by reference); by desiccation/inhibition-mediated DNA uptake (Potrykus et al., 1985). Through the application of techniques such as these, cells may be stably or transiently transformed.

B. Vectors

Vectors may find use with the current invention, for example, in the transformation of a host cells with a nucleic acid sequence encoding a chimeric polypeptides. The term "vector" is used to refer to a carrier nucleic acid molecule into which a nucleic acid sequence can be inserted for introduction into a cell where it can be replicated. A nucleic acid sequence can be "exogenous," or "heterologous", which means that it is foreign to the cell into which the vector is being introduced or that the sequence is homologous to a sequence in the cell but in a position within the host cell nucleic acid in which the sequence is ordinarily not found. Vectors include plasmids, cosmids and viruses (e.g., bacteriophage). One of skill in the art may construct a vector through standard recombinant techniques, which are described in Maniatis et al., 1988 and Ausubel et al., 1994, both of which references are incorporated herein by reference.

The term "expression vector" refers to a vector containing a nucleic acid sequence coding for at least part of a gene product capable of being transcribed. In some cases, RNA molecules are then translated into a polypeptide (e.g., a chimeric polypeptide). Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202, U.S. Pat. No. 5,928,906, each incorporated herein by reference).

Naturally, it will be important to employ a promoter and/or enhancer that effectively directs the expression of the DNA segment in the cell type chosen for expression. One example of such promoter that may be used with the invention is the *E. coli* arabinose or T7 promoter. Those of skill in the art of molecular biology generally are familiar with the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

3. Multiple Cloning Sites

Vectors can include a multiple cloning site (MCS), which is a nucleic acid region that contains multiple restriction enzyme sites, any of which can be used in conjunction with standard recombinant technology to digest the vector (see Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Termination Signals

The vectors or constructs prepared in accordance with the present invention will generally comprise at least one termination signal. A "termination signal" or "terminator" is comprised of the DNA sequences involved in specific termination of an RNA transcript by an RNA polymerase. Thus, in certain embodiments, a termination signal that ends the production of an RNA transcript is contemplated. A terminator may be necessary in vivo to achieve desirable message levels.

Terminators contemplated for use in the invention include any known terminator of transcription described herein or known to one of ordinary skill in the art, including but not limited to, for example, rhp dependent or rho independent terminators. In certain embodiments, the termination signal may be a lack of transcribable or translatable sequence, such as due to a sequence truncation.

5. Origins of Replication

In order to propagate a vector in a host cell, it may contain one or more origins of replication sites (often termed "ori"), which is a specific nucleic acid sequence at which replication is initiated.

6. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

C. Host Cells

In the context of expressing a chimeric polypeptide, "host cell" refers to a cell, of any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. Host cells for use according to the embodiments include, without limitation, insect cells, mammalian cell (e.g., CHO cells), ciliate cells, yeast cells and bacterial cells.

For example, numerous prokaryotic cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE, La Jolla). Alternatively, bacterial cells such as *E. coli* LE392 could be used as host cells for bacteriophage.

Many host cells from various cell types and organisms are available and would be known to one of skill in the art. Similarly, a viral vector may be used in conjunction with a prokaryotic host cell, particularly one that is permissive for replication or expression of the vector. Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids and chimeric polypeptides of the embodiments.

D. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

In addition to the disclosed expression systems of the invention, other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

IV. Antibodies

Certain aspects of the embodiments provide antibodies that comprise the chimeric polypeptides of the embodiments. Thus such antibodies can engage the effector functions of Fcα and Fcγ receptors. Such antibodies can be produced recombinantly, for example, by fusing chimeric polypeptides of the embodiments with an appropriate VH domain and expressing it with an appropriate Ig light chain. For example, an antibody of the embodiments can comprise a chimeric polypeptide of the embodiments and the CDRs of a known therapeutic antibody such as one of those in Table A below.

TABLE A

| Therapeutic antibodies: | |
|---|---|
| Antibody | Indication |
| Cancer | |
| Alemtuzumab | B-CLL, CTCL, T-cell lymphoma |
| Bevacizumab | Certain metastatis cancers (colon, lung, renal, glioblastoma) |
| Brentuximab vedotin | Anaplastic large cell lymphoma (ALCL), Hodgkin lymphoma |
| Catumaxomab | Malignant ascites |
| Cetuximab | Colorectal cancer, Head and neck cancer |
| Clivatruzumab tetraxetan | Pancreatic cancer |
| Denosumab | Postmenopausal osteoporosis, Solid tumor bony metasteses |
| Gemtuzumab ozogamicin | Acute myelogenous leukemia |
| Ibritumomab tiuxetan | B cell non-Hodgkin's lymphoma |

TABLE A-continued

| Therapeutic antibodies: | |
|---|---|
| Antibody | Indication |
| Ipilimumab | Melanoma |
| Ofatumumab | Chronic lymphocytic leukemia |
| Panitumumab | Colorectal cancer |
| Pertuzumab | HER2-positive metastatic breast cancer |
| Rituximab | Non-Hodgkin lymphoma |
| Tositumomab | Follicular lymphoma |
| Trastuzumab | Breast cancer |
| Immune | |
| Adalimumab | Several auto-immune disorders |
| Basiliximab | Transplant rejection |
| Belimumab | Systemic lupus erythematosus |
| Canakinumab | Cryopyrin-associated periodic syndrome (CAPS) |
| Certolizumab pegol | Crohn's disease, rheumatoid arthritis |
| Daclizumab | Transplant rejection |
| Golimumab | Rheumatoid arthritis, Psoriatic arthritis, Ankylosing spondylitis |
| Infliximab | Several auto-immune disorders |
| Mepolizumab | Asthma, white blood cell diseases |
| Muromonab-CD3 | Transplant rejection |
| Natalizumab | Multiple sclerosis, Crohn's disease |
| Omalizumab | Allergy-related asthma |
| Tocilizumab (or Atlizumab) | Rheumatoid arthritis |
| Ustekinumab | Plaque psoriasis |
| Other | |
| Ranibizumab | Macular degeneration |
| Abciximab | Cardiovascular disease; angioplasty |
| Eculizumab | Paroxysmal nocturnal hemoglobinuria, aHUS |
| Palivizumab | RSV infection |

V. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Design of the IgG-IgA Chimeras

In order to recapitulate binding affinity for FcαRI in an IgG1 scaffold, several domain swap variants were constructed by replacement of residues in the IgG1 CH2 and CH3 domains with the corresponding IgA1 sequences. Mutant B replaces IgG1 residues 336-443 (KGQPR . . . LSPGK, Kabat numbering; SEQ ID NO: 10) with IgA1 residues 335-444 (SGNTF . . . KTIDR; SEQ ID NO: 9). This mutant was generated as a negative control for ELISA assays and has previously been shown not to have affinity for the FcαRI receptor (Pleass et al., 1999). Mutant C replaces IgG1 residues 336-443 (KGQPR . . . LSPGK; SEQ ID NO: 10) and 242-254 (PKPKDTLMISRTPE; SEQ ID NO: 16) with IgA1 residues 336-443 (SGNTF . . . KTIDR; SEQ ID NO: 9) and 245-257 (PALEDLLLGSEAN; SEQ ID NO: 14), respectively. In the IgA:FcαRI crystal structure the α1 IgA CH2 domain loop (PALEDLLLGSEAN; SEQ ID NO: 14) makes extensive contacts with the FcαRI receptor (Herr et al., 2003). The entire α1 loop (PALEDLLLGSEAN; SEQ ID NO: 66) from IgA was substituted into IgG in order to preserve native contacts. Mutant D replaces IgG1 residues 336-443 (KGQPR . . . LSPGK; SEQ ID NO: 10) and 242-254 (PKPKDTLMISRTPE; SEQ ID NO: 16) with IgA1 residues 336-443 (SGNTF . . . KTIDR; SEQ ID NO: 9) and 245-257 (PALEDLLLGSEAN; SEQ ID NO: 14), respectively, but contains an additional glycine following IgA1 residue 257 (FIG. 1A). The glycine residue was added to ensure that the length of the modified IgG CH2 polypeptide is consistent with that of the authentic IgG, thus preserving secondary structure contacts.

Example 2—Construction and Expression of Fc Domain IgA/G Chimeras

Figure 2:
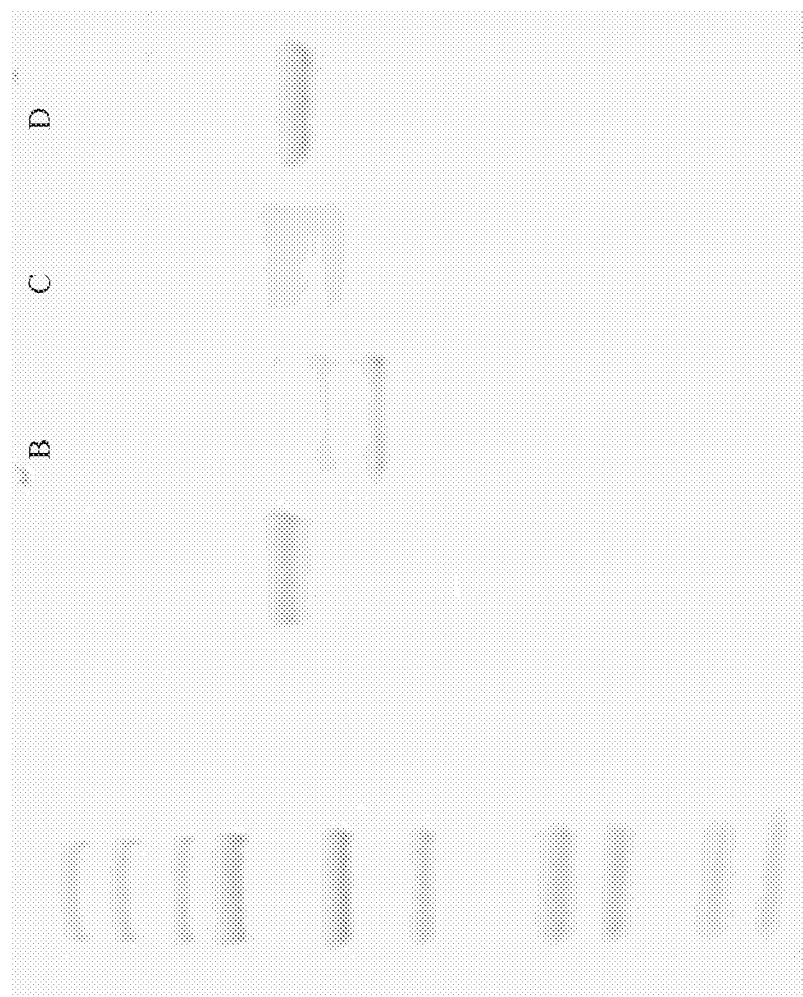
FIG. 2: Show the results of SDS-PAGE (4%-20%) analysis of chimeric Fc polypeptides of the embodiments.

All plasmids and primers are described in Tables 1 and 2. DNA sequences for mutants B-D were assembled by PCR using oligonucleotide primers synthesized in house shown in Table 2 (Mutant B—WK188, 190, 194, 196, 198, 200, 202, 204, 206, 207; Mutant C—WK188, 191, 194, 196, 198, 200, 202, 204, 206, 207; Mutant D—WK188, 192, 194, 196, 198, 200, 202, 204, 206, 207). Each of the IgG mutants were then cloned into pMaz-FcγRI-His by Overlap Extension PCR. Double stranded megaprimers for mutant B (pMaz-IgH MutB) were generated with primers WK366 and WK209 and for both mutants C (pMaz-IgH MutC) and D (pMaz-IgH MutD) using primers WK370 and WK209. Following DpnI digestion and transformation into JUDE-1 cells, plasmid DNA was prepared (Qiagen, HiSpeed Plasmid Midi Kit) for transfection. 293Fectin Transfection Reagent (Invitrogen) was used to transfect HEK293F (Invitrogen) cells cultured in GIBCO FreeStyle™ 293 Expression Medium (Invitrogen) in accordance with the manufacturer's instructions. Five to six days after transfection, the cell suspension was centrifuged at 2,000 rpm for 10 min to recover the supernatant fraction. PBS (25×) was added to a final concentration of 1× in addition to 10 mM imidazole, and the solution was passed through Ni-NTA affinity columns for IMAC chromatographic isolation of the Fc proteins. Bound protein was washed with PBS containing 20 mM imidazole and eluted in PBS with 250 mM imidazole directly into Amicon 10 kDa spin columns for buffer exchange and concentration. SDS-PAGE analysis showed good assembly for mutant D but not for mutants B and C indicating the addition of the glycine to the CH2 loop in the IgG structure is likely required for good assembly (FIG. 2).

Example 3—Binding Properties to FcγRs

Mammalian Expression of Fc Receptors.

FcαRI-GST, FcγRI-GST, FcγRIIa-R131-GST, FcγRIIb-GST, and FcγRIIIa-F158-GST were produced by transient transfection of HEK293F cells (Invitrogen) using the pMAZ-IgH (U.S. Pat. No. 8,043,621, incorporated herein by reference) derived expression vectors described in Table 1. Glutathione Sepharose (GE Healthcare) affinity chromatography was used according to the manufacturer's instructions to purify each variant to >95% purity as assessed by SDS-PAGE. PBS at 25× concentration was added to the filtered supernatants six days after transfection to make a final PBS concentration of 1×, and the mixture was passed twice over the column. The column was washed with 100 mL of 1×PBS to remove nonspecifically bound protein. Four milliliters of 1×PBS containing 10 mM reduced glutathione was used for elution into 10 kDa filter columns.

ELISA Testing.

ELISA plates (Qiagen) were coated with 4 μg/mL of each of the mutant Fc domains in 1×PBS (pH 7.4) overnight at 4° C. The next day the plates were blocked for 2 hours at room temperature with 2% milk in 1×PBS containing 0.05% Tween (PBST) and washed three times in PBST at pH 7.4. To the first well, 66 μL of 20 μg/mL of either FcγRI-GST, FcγRI-GST, FcγRIIa-R131-GST, FcγRIIb-GST, or FcγRIIIa-F158-GST dissolved in PBS with 2% milk (PBSM) was added followed by 1:4 serial dilution. After 1 h of incubation at room temperature, the plates were washed and 50 μL PBSM was added containing 1:5000 goat anti-GST HRP (GE Healthcare) for 1 hour. To develop the plates, the wells were washed 3× with PBST, 50 μL TMB substrate was added per well (Thermo Scientific), 50 μL of 1 M $H_2SO_4$ was added to neutralize, and the absorbance at 450 nm was recorded. Mutant D was shown to have binding for both FcαRI (FIG. 3) and the Fcγ class of receptors (FIGS. 4-6). FcαRI binding was shown to be reduced compared to wild-type glycosylated IgA, whereas affinity for FcγRI was largely retained. Mutant D has reduced affinity to FcγRIIb but only marginally reduced affinity to FcγRIIa.

Example 4—Alanine Mutagenesis

Figure 7:
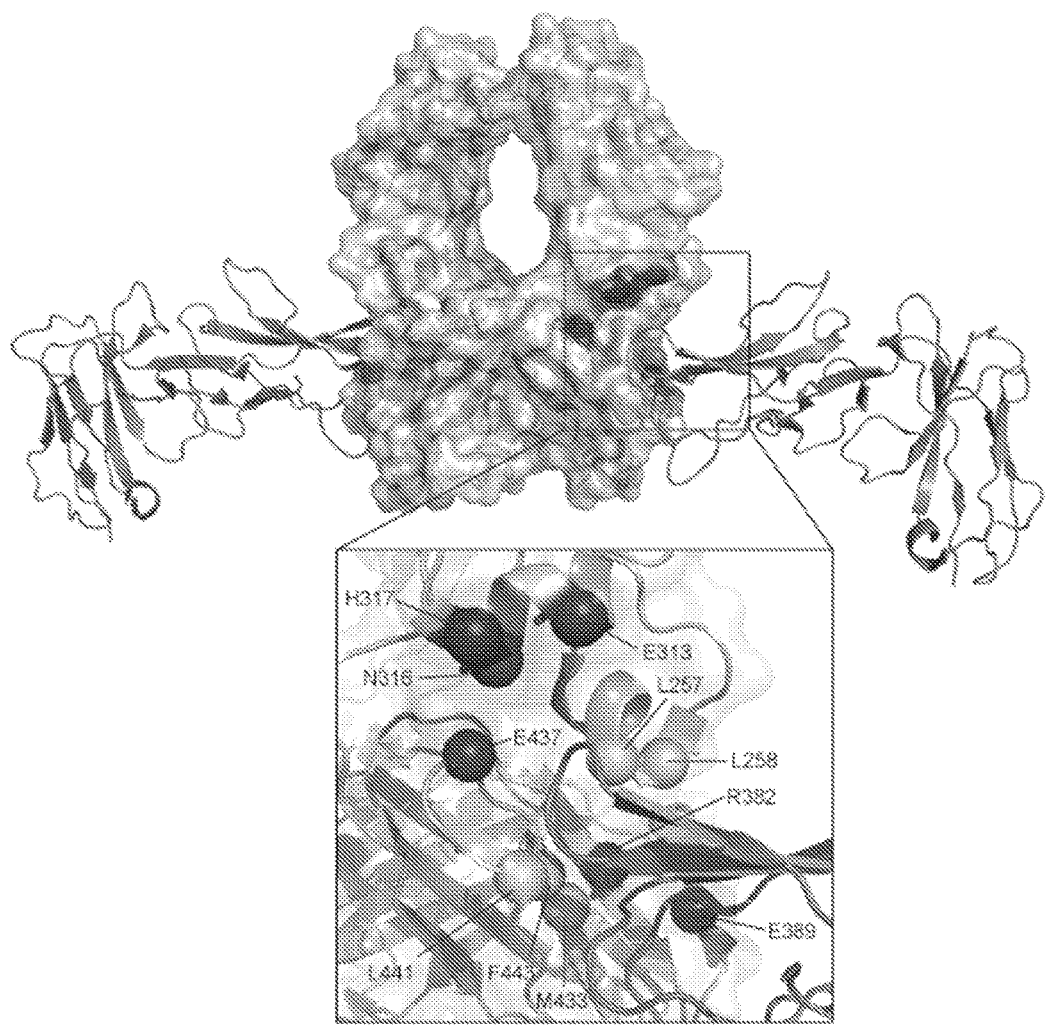
FIG. 7: Sites mutated to alanine to scan the binding pocket of FcαRI in IgA for the relative binding contribution of each position. Picture shows a model of the IgA binding pocket.
Figure 8:
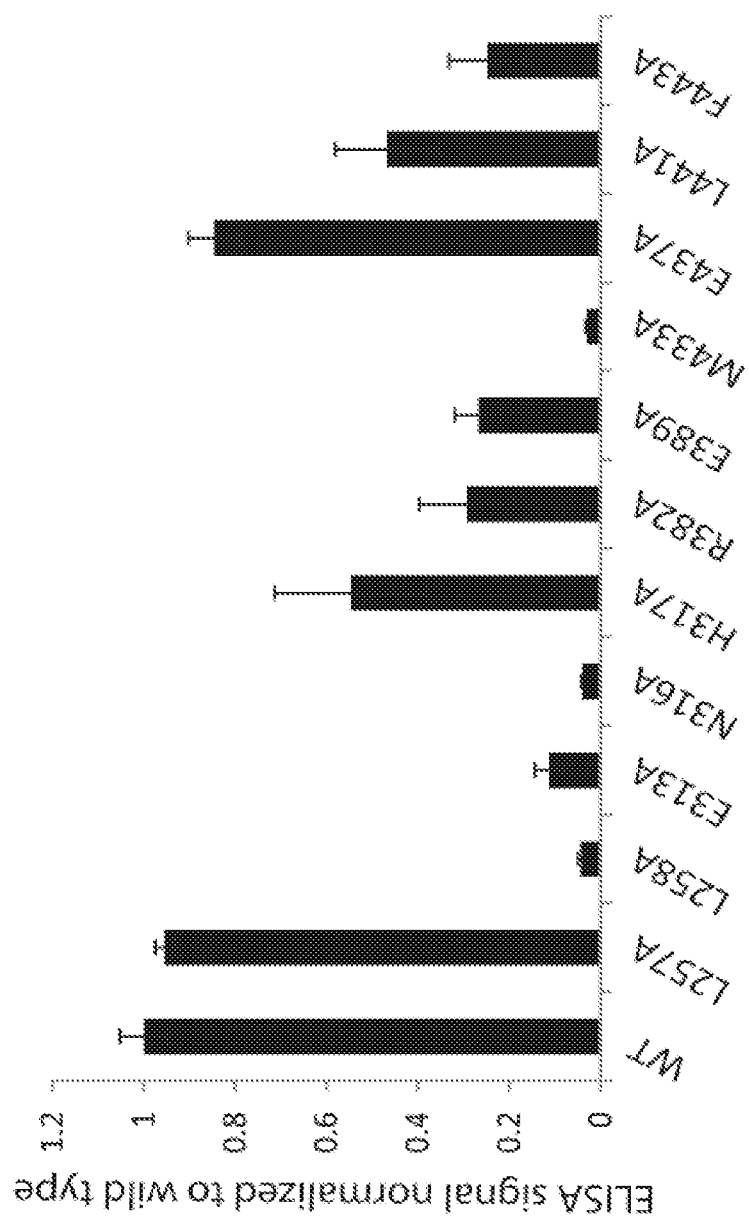
FIG. 8: Graph shows the results of ELISA analysis of FcαRI binding to IgA Fc domains containing alanine scanning point mutations. Signal has been normalized to a wild type IgA Fc domain.

Alanine scanning mutagenesis on IgA was performed to help identify residues important for binding to FcαRI. Based on crystal structure and Rosetta modeling, 11 sites in the IgA Fc domain were selected for alanine scanning mutagenesis (FIG. 1B; FIG. 7). The following IgA mutants containing L257A (constructed using primers TKA4, TKA5), L258A (constructed using primers TKA6, TKA7), E313A (constructed using primers TKA8, TKA9), N316A (constructed using primers TKB1, TKB2), H317A (constructed using primers TKB3, TKB4), R382A (constructed using primers TKB7, TKB8), E389A (constructed using primers TKC1, TKC2), M433A (constructed using primers TKC5, TKC6), E437A (constructed using primers TKD1, TKD2), L441A (constructed using primers TKD5, TKD6), and F443A (constructed using primers TKE1, TKE2) were generated using Quickchange PCR with pTrc-DsbA IgA CH2 CH3 as the DNA template. Cloning into the mammalian expression vector pMaz-IgH was achieved by Gibson assembly (Gibson et al., 2009) after amplification of the individual Fc domains (Primers WK346 and WK347) and amplification of the pMaz-IgH-FcγRI-His backbone (Primers WK212 and WK314). Following transformation into E. coli JUDE-1 cells, the mutant genes were sequenced and DNA was prepared for transient transfection in HEK293F cells (Invitrogen). IgA was purified as in Example 2 above. ELISA analysis was used to evaluate binding to FcαRI. Briefly, each IgA variant was coated at 4 μg/mL onto ELISA plates (Qiagen), then FcαRI-GST at 10 μg/mL was added to the first well and serially diluted before detection with goat anti-GST HRP as described in Example 2. Alanine substitutions at positions 258, 313, 316, and 433 resulted in very significant decrease in binding activity (FIG. 8). Moderate reductions in affinity occurred when mutations were made at positions 382, 389, and 443, while little effect on binding was observed at positions 257, 317, 437 and 441. Residues that have a relatively modest effect on binding to the receptor may be optimized by mutagenesis and screening to impart higher binding affinity for the IgG/A chimera, mutant D, onto FcαRI.

Figure 9:
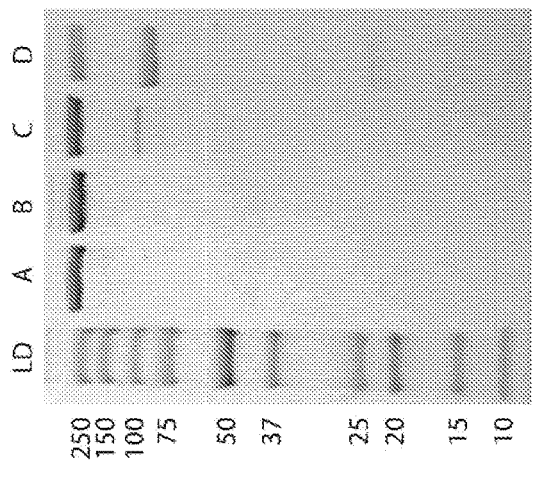
FIG. 9: Figure shows results of a 4-20% SDS-PAGE separation of full length antibodies expressed from HEK293F cells. Lane A trastuzumab IgG, Lane B trastuzumab IgG N297D, Lane C trastuzumab MutD, Lane D trastuzmab IgA

Example 5—Construction and Expression of Full Length IgA/G Chimeras and Control Antibodies All plasmids and primers are described in Tables 1 and 2. Plasmids for expression of wild type trastuzumab IgG heavy chain (pMaz-IgH-trastuzumab), trastuzumab kappa light chain (pMaz-IgL-trastuzumab) and trastuzumab IgG N297D heavy chain (pMaz-IgH-N297D-trastuzumab) were constructed as described previously (Jung et al. 2012). Inserts for trastuzumab IgA heavy chain (Primers WK353 and WK354) and trastuzumab MutD heavy chain (Primers WK364 and WK 356) were amplified for cloning into the pMaz-IgH (U.S. Pat. No. 8,043,621) expression plasmid by OLE PCR. In each case plasmid pMaz-IgH-trastuzumab was used as the DNA template. After transformation into E. coli JUDE-1 cells, colonies were isolated for sequencing and DNA was prepared for each heavy chain and combined with an equal mass of light chain plasmid for transient transfection in HEK293F cells (Invitrogen). Five to six days after transfection, the cell suspension was centrifuged at 2000 rpm for 10 min to recover the supernatant fraction. Trastuzumab IgG and trastuzumab IgG N297D were purified over protein A affinity columns whereas trastuzumab IgA and trastuzumab MutD were purified over protein L affinity columns. Briefly, the supernatants were passed through 0.22 µm filters before addition to polypropylene columns packed with either Protein A high capacity agarose resin (Thermo Scientific) or Protein L agarose resin (Invivogen). The resulting flow-through was collected and passed twice more through the column before any unbound protein was washed away with >10 CV (Column Volume) of 1×PBS. All antibodies were eluted with 3 ml of 100 mM citrate buffer (pH 3.0) and immediately neutralized with 1 ml of 1 M Tris (pH 8.0). Samples were buffer-exchanged into 1×PBS using Amicon Ultra-4 (Millipore) spin columns with a 10 kDa cutoff and the purity of purified samples was assessed by 4-20% gradient SDS-PAGE gel (NuSep). SDS-PAGE analysis revealed better assembly of MutD than IgA as seen in FIG. 9.

Example 6—Binding Properties of Full Length Antibodies to FcγRs

Mammalian Expression of Monomeric FcγRIIa and FcγRIIb Receptors.

The genes encoding monomeric low affinity Fc receptors (FcγRIIa and FcγRIIb) were generated by Gibson assembly as follows: The backbone of the pcDNA3.4 vector (Invitrogen) was amplified in two segments; a 2.5 kb fragment (using primers WK426 and WK463) and a 3.5 kb fragment (using primers WK425 and WK464). The insert for FcγRIIa-R131 was created using primers WK448 and WK461 with plasmid pMaz-IgH-FcγRIIa$_{R131}$-His (Jung et al. 2012) as a template. Similarly the insert for FcγRIIb was generated using primers WK450 and WK462 with pMaz-IgH-FcγRIIb-GST (Jung et al. 2012) as a template. Each insert was combined with the two backbone segments for 60 minutes at 50° C. in a Gibson master mix (Gibson et al. 2009), to create the plasmids pcDNA3.4-FcγRIIb-His and pcDNA3.4-FcγRIIaR131-His, before transformation into E. coli. The respective plasmids for FcγRIIa-R131 and FcγRIIb expression were transfected for 5-6 days using Expi293F cells (Invitrogen). Purification was performed by Ni-NTA affinity chromatography as described previously and expression confirmed by 4-20% SDS page gel.

SPR Affinity Measurements.

Figure 10:
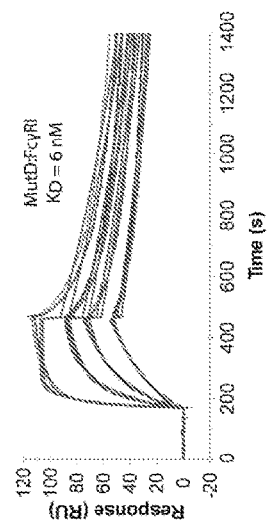
FIG. 10: SPR kinetic analysis of MutD binding to soluble FcγRI as fit by a 1:1 Langmuir isotherm model.

A Biacore 3000 instrument (GE Healthcare) was used to determine $K_D$ values for MutD binding to FcγRI, FcγRIIa-R131, FcγRIIb and FcαRI. In all cases amine coupled BSA reference channels were used to subtract nonspecific binding signal. To determine MutD affinity for FcγRI, CM5 chips (GE Healthcare) were covalently immobilized with trastuzumab MutD by amine coupling at pH 5.0. Concentrations ranging from 400 nM to 0 nM of soluble FcγRI (R&D systems) were flowed in duplicate across the chip at 20 µl/min. The resulting binding profiles were fit to a 1:1 Langmuir isotherm model with local Rmax using Biaevaluation 3.0 software. The chip was regenerated after each binding event with 100 mM Sodium Citrate pH 3.0 with a contact time of 30 seconds. MutD retains close to wild type affinity (6 nM) for FcγRI when compared to values previously reported, as seen in FIG. 10 (Jung et al. 2010).

Figure 11:
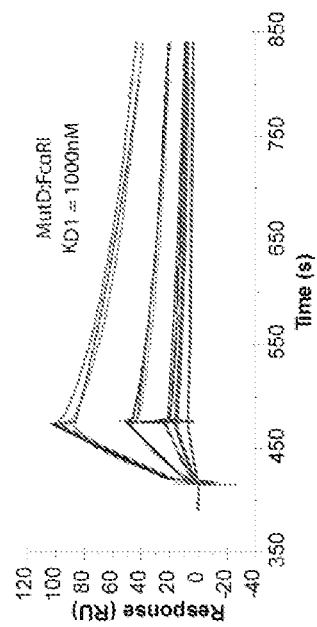
FIG. 11: SPR kinetic analysis of MutD binding to soluble FcαRI-GST as fit by a 2:1 bivalent analyte model.
Figure 12:
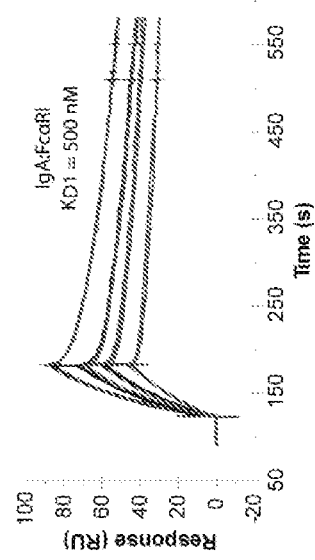
FIG. 12: SPR kinetic analysis of IgA binding to soluble FcαRI-GST as fit by a 2:1 bivalent analyte model.

For evaluation of FcαRI binding to trastuzumab MutD and trastuzumab IgA, CM5 chips were immobilized with each of the antibodies by amine coupling. Concentrations ranging from 300 nM to 0 nM of soluble dimeric FcαRI-GST were flowed in duplicate across the chip at 30 µl/min. A three step regeneration was used after each binding event; 2 minutes of 50 mM glycine buffer pH 4.0, 2 minutes of 50 mM glycine pH 9.5 and 2 minute of 3 M NaCl. Because of the dimeric nature of the receptor, the data was fit using a 2:1 bivalent analyte model with Biaevaluation 3.0 software. Trastuzumab MutD, as shown in the sensorgram in FIG. 11, displays significant binding for FcαRI (1000 nM) within the range of what was detected for trastuzumab IgA (500 nM) shown in FIG. 12.

Figure 13:
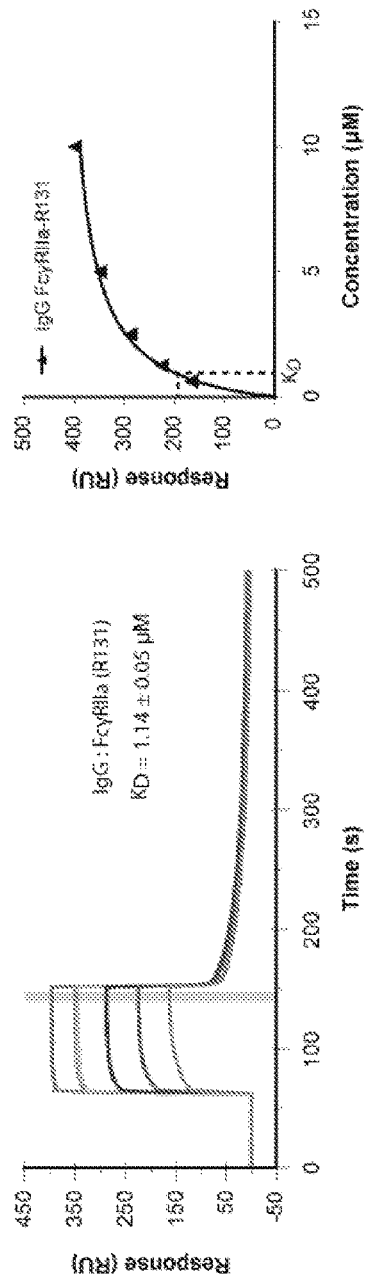
FIG. 13: SPR equilibrium analysis of IgG binding to soluble monmeric FcγRIIaR131 as fit by a 1:1 Langmuir isotherm model.
Figure 14:
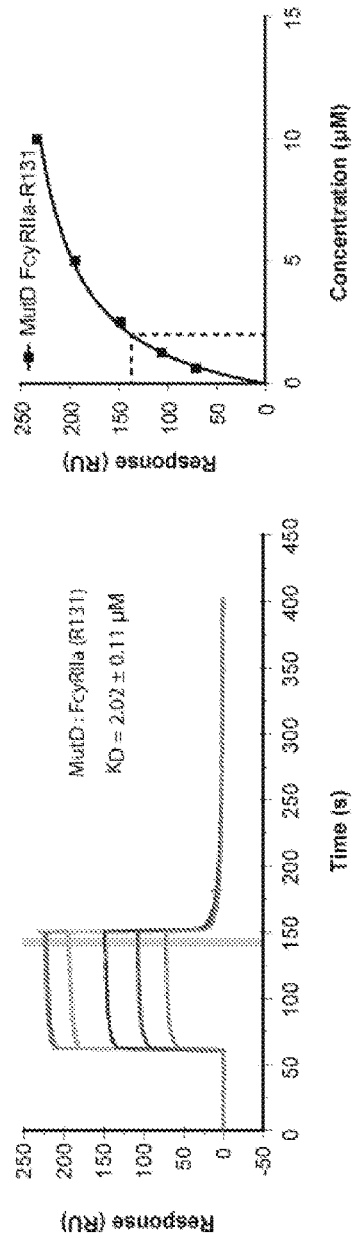
FIG. 14: SPR equilibrium analysis of MutD binding to soluble monmeric FcγRIIaR131 as fit by a 1:1 Langmuir isotherm model
Figure 15:
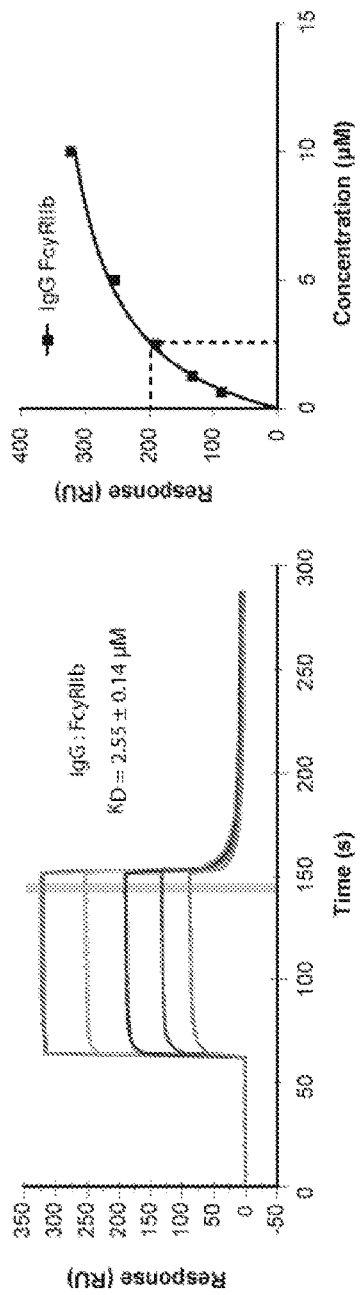
FIG. 15: SPR equilibrium analysis of IgG binding to soluble monmeric FcγRIIb as fit by a 1:1 Langmuir isotherm model.
Figure 16:
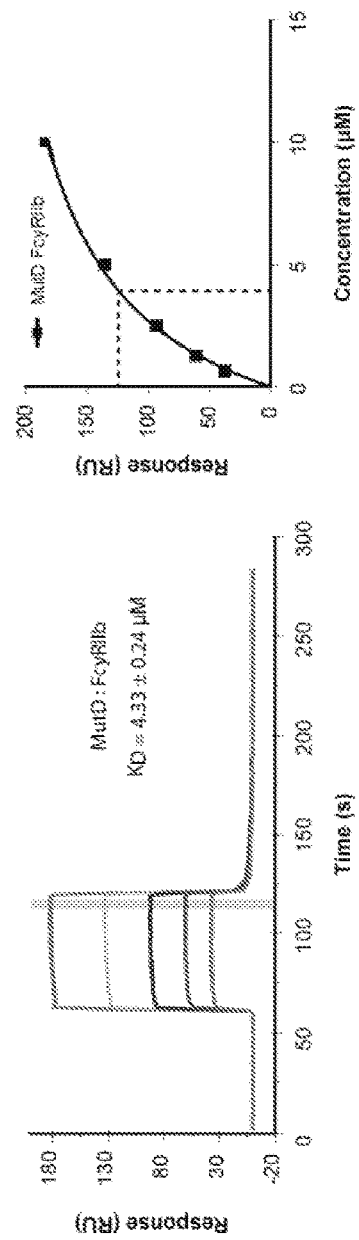
FIG. 16: SPR equilibrium analysis of MutD binding to soluble monmeric FcγRIIb as fit by a 1:1 Langmuir isotherm model.

For affinity determination of FcγRIIa and FcγRIIa-R131 binding to trastuzumab MutD and trastuzumab IgG, antibodies were immobilized by amine coupling to CM5 chips at pH 5.0 in 50 mM Sodium Acetate buffer. Concentrations ranging from 10 µM to 0 µM of monomeric FcγRIIb and FcγRIIa-R131 were flowed in duplicate across the chip at 20 µl/min until an equilibrium state was achieved. Dissociation was performed using an 8 minute step in the HBS-EP running buffer (GE Healthcare). A 1:1 Langmuir isotherm model was fit to the equilibrium data to obtain $K_D$ values for each of the interactions. As indicated in FIG. 13 FcγRIIb displays and affinity of 4.33 µM for MutD and a higher 2.55 µM affinity for IgG, presented in FIG. 14. MutD also retains an affinity of 2.02 µM for the low affinity R131 allele of FcγRIIa as seen in FIG. 15 in comparison to 1.14 µM for binding of this receptor to IgG as seen in FIG. 16.

Example 7—Antibody Dependent Cell Cytotoxicity Assays for the Killing of Cancer Cells by the Engineered Antibodies and Using Neutrophils as the Effector Cells ADCC Assays.

Figure 17:
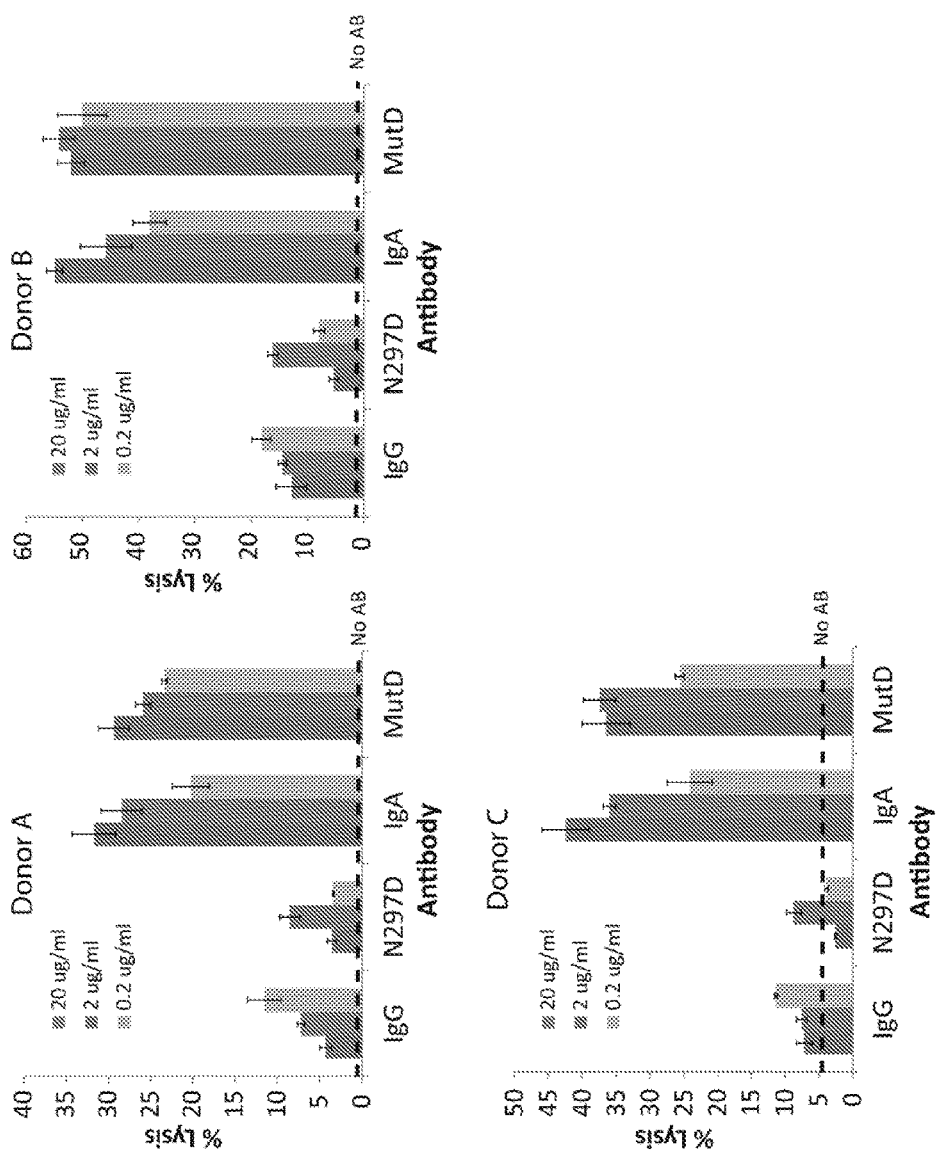
FIG. 17: Graphs show neutrophil killing of Her2+SkBR-3 cells by ADCC using IgG, aglycosylated IgG N297D, IgA and MutD trastuzumab variants. Cells were seeded at a ratio of 80:1 neutrophils to tumor cells. Bars in the graph indicate the results with decreasing concentration of the indicated antibodies (20, 2 or 0.2 μg/ml) from left to right.
Figure 18:
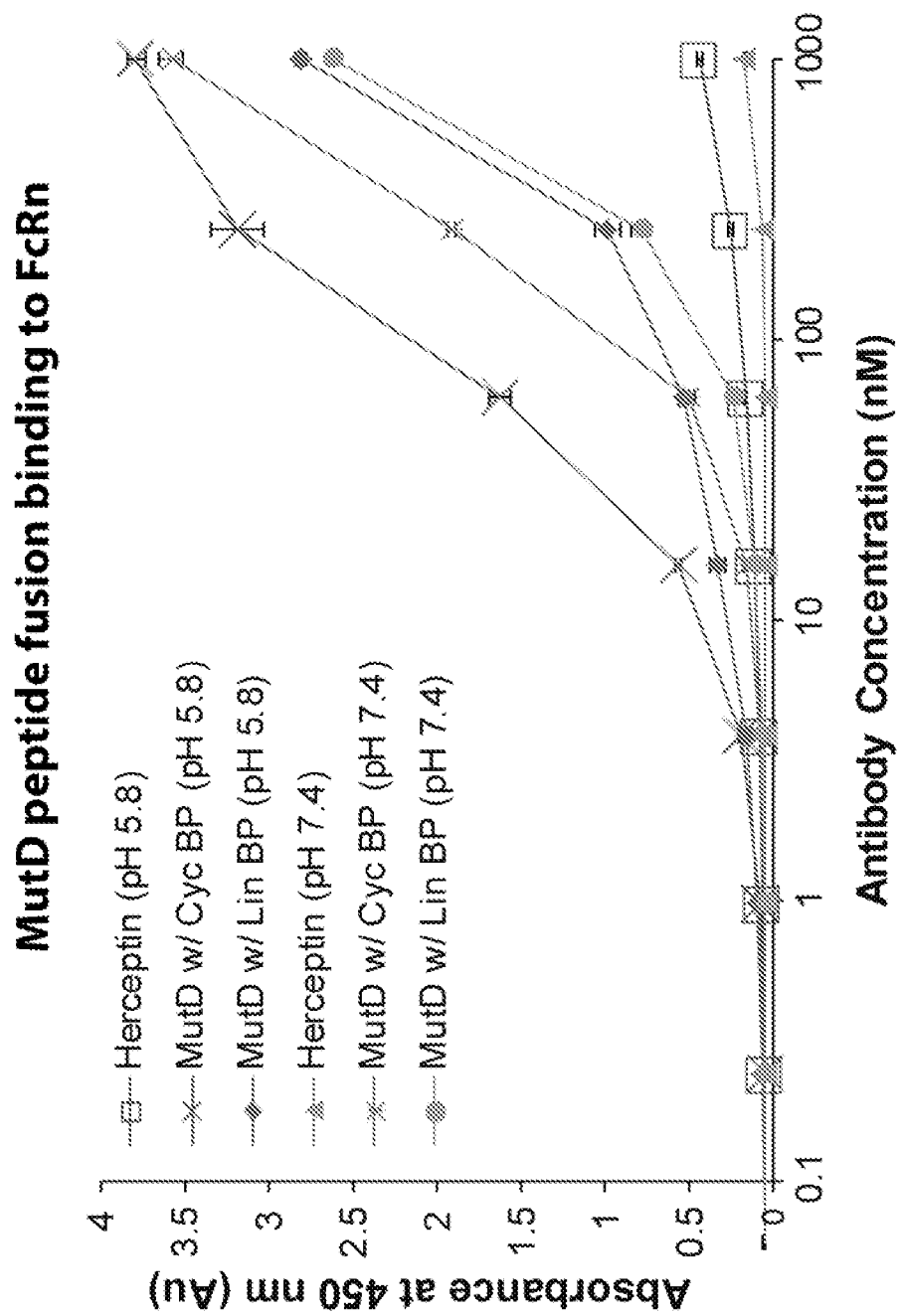
FIG. 18: Graph show the results of ELISA analysis of FcRN binding to MutD fusions with cyclic or linear C-terminus peptides at pH 7.4 and pH 5.8.

Human neutrophils were isolated from Heparin-treated fresh human blood gathered from anonymous donors (IRB protocol 2012-08-0031) on the day prior to the ADCC assay. 10 ml of blood was diluted 1:1 with PBS (Mediatech) and layered over 13 ml of room temperature Histopaque 1077 (Invitrogen) in 50 ml conical tubes. The mixture was centrifuged at 2500 rpm for 30 minutes at 25° C. with no brake during the deceleration phase. Serum, Histopaque and mononuclear cells were discarded. The pellet was resuspended in 4° C. cold shock buffer (155 mM Ammonium Chloride, 10 mM Potassium Bicarbonate and 0.1 mM EDTA) and incubated on ice for 10 minutes to lyse the red blood cells. The neutrophil fraction was isolated by centrifuging at 1300 rpm for 7 minutes and washing twice with 50 ml PBS. After the final wash, the neutrophils were resuspended in RPMI media containing 10% FBS as well as 50 ng/ml IFN-γ (Peprotech). The cells were cultured overnight at a concentration of 5×10$^6$ cells/ml in a 24 well plate under a humidified atmosphere of 5% $CO_2$. The following day expression of FcγRI and FcαRI was determined by FACS to confirm activation. Meanwhile, SkBR-3 tumor cells (ATCC) were cultured in McCoy's 5a media containing 10% FBS (Invitrogen) and Penicillin-Streptomycin (Invitrogen). On the day of the assay the tumor cells were recovered by trypsinization and labeled for 90 minutes with Cr51 (Perkin Elmer) in a 1 ml volume at a density of $1 \times 10^6$ cells/ml. The tumor cells were washed 3 times in RPMI containing 10% FBS and seeded in 96 well v bottom plates at 5000 cells/well. Antibody variants at various concentrations were added to opsonize the tumor cells for 30 mins at 37° C. Neutrophils were then added at a 1:80 tumor:effector cell ratio and the plates incubated at 37° C. with 5% $CO_2$ for 4 hours. Supernatants were recovered and 50 µl was added to Uncoated Scintiplate-96 plates (PerkinElmer). After overnight drying the plates were read in a MicroBeta scintillation counter (PerkinElmer). The ADCC assays presented in FIG. 17 show trastuzumab MutD is able to activate neutrophils to kill SkBR3 breast cancer tumor cells. In contrast, clinical grade trastuzumab cannot mediate killing of SkBR-3 cells with neutrophils as effectors. Trastuzumab MutD displayed a killing efficiency towards SkBr3 breast cancer cells similar to that of trastuzumab IgA comprising the Fab domain of trastuzumab fused to an IgA Fc domain. Unlike trastuzumab MutD which binds to Fcγ receptors as described in Example 6, trastuzumab IgA shows no binding to the Fcγ receptors.

Example 8—Conjugation of MutD with a FcRn Binding Peptide

Mammalian expression of FcRn peptide fusion to MutD: In order to reintroduce FcRn Binding to the MutD framework a C-terminal fusions with either a linear (QRFVTGH-FGGLYPANG; SEQ ID NO: 67) or a cyclic binding peptide (QRFCTGHFGGLHPCNG; SEQ ID NO: 68) were generated by Gibson assembly (Sockolosky et al. 2012). The linear peptide insert was created using primers JL-GS-L-Rn 1 and JL-GS-L-Rn 2 and the cyclic peptide insert was generated with JL-GS-C-Rn 1 and JL-GS-L-Rn 2 primers. The vector backbone was created by amplifying a 6.5 kb fragment from pcDNA3.4-IgH-Trastuzumab-MutD using primers JL-Gibson R and JL-Gibson F. Following transformation into *E. coli* and sequencing to verify cloning success the linear and cyclic variants were transfected into Expi293 cells as above. After 5 days of culture the proteins were isolated by Protein L chromatography as described in Example 5 and eluted in 100 mM pH 2.7 glycine HCl.

Figure 19:
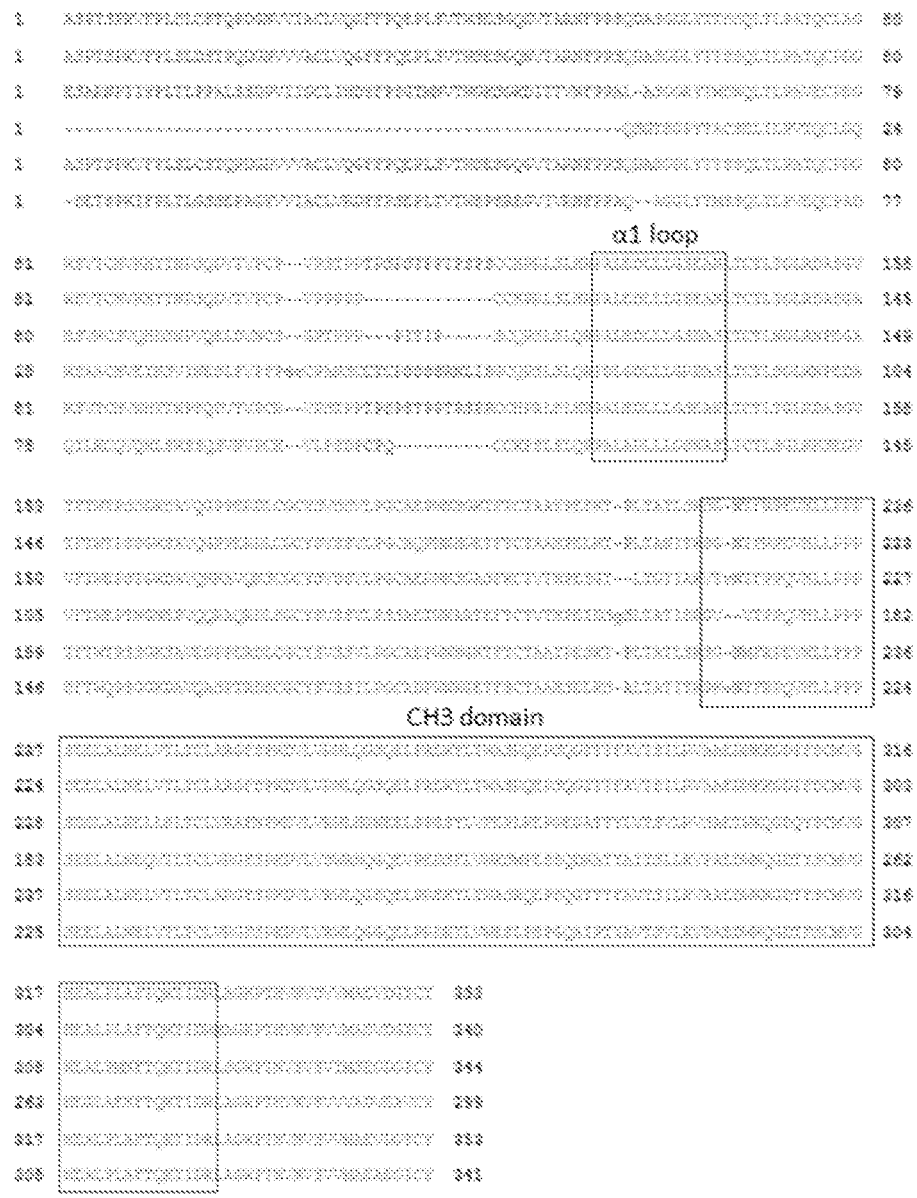
FIG. 19: An example alignment showing various mammalian IgA Fc domains with the locations of the CH2 α1 loop and CH3 domains indicated. Sequences in the alignment from top to bottom include those from the human IgA1 Fc (SEQ ID NO: 77); human IgA2 Fc (SEQ ID NO: 78); mouse IgA Fc (SEQ ID NO: 79); rabbit IgA Fc (SEQ ID NO: 80); gorilla IgA Fc (SEQ ID NO: 81); and pig IgA Fc (SEQ ID NO: 82).

ELISA Assay:

ELISA plates were coated with 4 µg/ml FcRn in PBS overnight. The following day wells were blocked with PBST containing a 2% milk solution for 2 hours at room temperature and washed 3× with PBST at pH 7.4. To the first well antibody variant was added at 140 µg/ml in either pH 7.4 PBS or pH 5.8 PBS with 40 mM MES and serially diluted by a factor of 4. After 1 hour at room temperature the plates were washed 3× with either pH 7.4 PBS or pH 5.8 PBS with 40 mM MES respectively depending on the pH at which the antibody was bound. The presence of antibody was detected by 1 hour incubation with a 1:5000 dilution of goat anti-human Cκ HRP in PBST with 2% milk, washing with pH 7.4 PBS or pH 5.8 PBS with 40 mM MES buffer and development with 50 ul TMB substrate. The reaction as quenched with 50 ul 1M $H_2SO_4$ was added to neutralize, and the absorbance at 450 nm was recorded. The cyclic peptide exhibited the highest binding to FcRn at both pH 5.8 and pH 7.4 with higher binding observed at the lower pH. The linear peptide also showed higher binding than wild type IgG at each pH as shown in FIG. 19. The increased affinity over wild type IgG is likely caused by the improved avidity of this construct.

TABLE 1

Primers used in this study
(provided as SEQ ID NOs: 17-53)

| Primer Name | Primer nucleotide sequence (5' → 3') |
|---|---|
| JL-Gibson F | TGAGCGGCCGCTCGAGGC (SEQ ID NO: 40) |
| JL-Gibson R | TTTGCCCGCCAGCCTGTCGATGGTCTTCTGGGTGAA (SEQ ID NO: 41) |
| JL-GS-C-Rn-1 | CGACAGGCTGGCGGGCAAAGGCGGCGGCGGCAGCCAGAG ATTCTGCACCGGCCACTTCGGCG (SEQ ID NO: 42) |
| JL-GS-C-Rn-2 | GCCTCGAGCGGCCGCTCAGCCGTTGCAGGGGTGCAGGCC GCCGAAGTGGCCGGTGCA (SEQ ID NO: 48) |
| JL-GS-L-Rn-1 | CGACAGGCTGGCGGGCAAAGGCGGCGGCGGCAGCCAGAG ATTCGTGACCGGCCACTTCGGCG (SEQ ID NO: 49) |
| JL-GS-L-Rn-2 | GCCTCGAGCGGCCGCTCAGCCGTTGGCGGGGTACAGGCC GCCGAAGTGGCCGGTCAC (SEQ ID NO: 51) |
| TKA4 | GCGTTGGAAGACCTTGCGCTTGGTAGCGAAGCG (SEQ ID NO: 17) |
| TKA5 | CGCTTCGCTACCAAGCGCAAGGTCTTCCAACGC (SEQ ID NO: 18) |
| TKA6 | CGTTGGAAGACCTTCTGGCGGGTAGCGAAGCGAATCTG (SEQ ID NO: 19) |
| TKA7 | CAGATTCGCTTCGCTACCCGCCAGAAGGTCTTCCAACG (SEQ ID NO: 20) |
| TKA8 | CTGTCGGGTTGCGCAGCGCCGTGGAATCATGGC (SEQ ID NO: 21) |
| TKA9 | GCCATGATTCCACGGCGCTGCGCAACCCGACAG (SEQ ID NO: 22) |
| TKB1 | GGTTGCGCAGAACCGTGGGCGCATGGCAAAACATTCAC (SEQ ID NO: 23) |
| TKB2 | GTGAATGTTTTGCCATGCGCCCACGGTTCTGCGCAACC (SEQ ID NO: 24) |
| TKB3 | GCGCAGAACCGTGGAATGCGGGCAAAACATTCACCTG (SEQ ID NO: 25) |
| TKB4 | CAGGTGAATGTTTTGCCCGCATTCCACGGTTCTGCGC (SEQ ID NO: 26) |
| TKB7 | CGAAAGATGTTCTGGTGGCGTGGCTGCAGGGAAGCC (SEQ ID NO: 27) |
| TKB8 | GGCTTCCCTGCAGCCACGCCACCAGAACATCTTTCG (SEQ ID NO: 28) |
| TKC1 | TGCAGGGAAGCCAAGCGCTGCCCCGTGAAAAG (SEQ ID NO: 29) |
| TKC2 | CTTTTCACGGGGCAGCGCTTGGCTTCCCTGCA (SEQ ID NO: 30) |
| TKC5 | GATACGTTCAGCTGCGCGGTGGGCCATGAGGC (SEQ ID NO: 31) |
| TKC6 | GCCTCATGGCCCACCGCGCAGCTGAACGTATC (SEQ ID NO: 32) |

TABLE 1-continued

Primers used in this study (provided as SEQ ID NOs: 17-53)

| Primer Name | Primer nucleotide sequence (5' → 3') |
| --- | --- |
| TKD1 | ATGGTGGGCCATGCGGCACTTCCGCTG (SEQ ID NO: 33) |
| TKD2 | CAGCGGAAGTGCCGCATGGCCCACCAT (SEQ ID NO: 34) |
| TKD5 | GCCATGAGGCACTTCCGGCGGCCTTTACTCAAAAAC (SEQ ID NO: 35) |
| TKD6 | GTTTTTTGAGTAAAGGCCGCCGGAAGTGCCTCATGGC (SEQ ID NO: 36) |
| TKE1 | GAGGCACTTCCGCTGGCCGCGACTCAAAAAACTATT-GAT C (SEQ ID NO: 37) |
| TKE2 | GATCAATAGTTTTTTGAGTCGCGGCCAGCGGAAGT-GCCT C (SEQ ID NO: 38) |
| WK209 | CGAGGCTGATCAGCGAGCT (SEQ ID NO: 39) |
| WK314 | TGATCTAGAAGCTCGCTGATCAGCCTC (SEQ ID NO: 43) |
| WK346 | GCCTTTCTCTCCACAGGCGCGCACTCCGTGCCGAG-CACC CCCC (SEQ ID NO: 44) |
| WK347 | CGAGGCTGATCAGCGAGCTTCTAGATCAGTGATGGT-GAT GATGGTG TTTGCCC (SEQ ID NO: 45) |
| WK353 | GGACAATGGTCACCGTCTCCTCAGCGAGC-CCGACGTCTC C (SEQ ID NO: 46) |
| WK354 | GGCTGATCAGCGAGCTTCTAGATCATTTGCCCGCCA-GAC GATCAATAGTTTTTTGAGTAAAGGCCAGCGG (SEQ ID NO: 47) |
| WK364 | ACCGTCAGTCTTCCTCTTCCCCCCCGCGTTG-GAAGACCT TCTGCTTGGTAGCGAAGCGAATGGCGTCACAT-GCGTGGT GGTGGA (SEQ ID NO: 50) |
| WK366 | CCCATCGAGAAAACCATCTCCAAAGCCAGCG-GCAACACC TTCAGACC (SEQ ID NO: 52) |
| WK370 | TCAGTCTTCCTCTTCCCCCCAGCCCTGGAGGACTT-GCTG (SEQ ID NO: 53) |
| WK425 | TGAGCGGCCGCTCGAG (SEQ ID NO: 69) |
| WK426 | ACACTGGACACCTTTGAGCACAGC (SEQ ID NO: 70) |
| WK448 | CGCTGTGCTCAAAGGTGTCCAGTGTCAAGCTGCTC-CCCC AAAGGCTG (SEQ ID NO: 71) |
| WK450 | CGCTGTGCTCAAAGGTGTCCAGTGTACACCTGCA-GCTCC CCCAAAGG (SEQ ID NO: 72) |
| WK461 | GTGGTGATGGTGATGATGCCCCATTGGTGAAGAGCT-GCC C (SEQ ID NO: 73) |

TABLE 1-continued

Primers used in this study (provided as SEQ ID NOs: 17-53)

| Primer Name | Primer nucleotide sequence (5' → 3') |
| --- | --- |
| WK462 | GTGGTGATGGTGATGATGGGGAGCTTGGACAGT-GATGGT CAC (SEQ ID NO: 74) |
| WK463 | CGCCTTATCCGGTAACTATCGTCTTG (SEQ ID NO: 75) |
| WK464 | GACTCAAGACGATAGTTACCGGATAA (SEQ ID NO: 76) |

TABLE 2

Oligonucleotides used for gene assembly in this study (SEQ ID NOs: 54-65)

| Primer Name | Oligonucleotide sequence (5' → 3') |
| --- | --- |
| WK188 | TTTCTCTCCACAGGCGCGCACTCCGACAAAACTCACACAT-GCCC ACCGTGCCCAGCACCTGAACTCCTGGGGGGACCGTCAGTCT-TCC TCTTCC |
| WK190 | GGTCTTCGTGGCTCACGTCCACCACCACGCATGTGACCTCA-GGG GTCCGGGAGATCATGAGGGTGTCCT-TGGGTTTTGGGGGGAAGAG GAAGACTGACGGTCCC |
| WK191 | GGTCTTCGTGGCTCACGTCCACCACCACGCACGTCACGTTG-GCC TCGCTGCCCAGCAGCAAGTCCTCCAGGGCTGGGGGGAAGAG-GAA GACTGACGGTCCC |
| WK192 | GGTCTTCGTGGCTCACGTCCACCACCACGCACGTCACGC-CGTTG GCCTCGCTGCCCAGCAGCAAGTCCTCCA-GGGCTGGGGGAAGAG GAAGACTGACGGTCCC |
| WK194 | GTGGACGTGAGCCACGAAGACCCTGAGGTCAAGTTCAACTG-GTA CGTGGACGGCGTGGAGGTGCATAATGCCAAGACAAAGC-CGCGGG AGGAGCAGTAC |
| WK196 | GGAGACCTTGCACTTGTACTCCTTGCCATTCAGCCAGTC-CTGGT GCAGGACGGTGAGGACGCTGACCACACGGTACGTGCTGTTG-TAC TGCTCCTCCCGCGG |
| WK198 | GCAAGGAGTACAAGTGCAAGGTCTCCAACAAAGCCCTCCCA-GCC CCCATCGAGAAAACCATCTCCAAAGCCAGCGGCAACACCT-TCAG ACCCGAGGTGCATCTGC |
| WK200 | GCACGTCCTTGGGGCTGAAGCCCCTCGCAAGGCAGGT-GAGAGTG ACCAGCTCGTTCAGGGCGAGCTCCTCGCTGGGAGGGGGCA-GCAG ATGCACCTCGGGTCTGAAG |
| WK202 | CTTCAGCCCCAAGGACGTGCTCGTGAGGTGGCTGCA-GGGCTCCC AGGAGCTGCCCAGGGAGAAGTACCTGACCTGGGCCAGCAG-GCAG GAGCCCAGCCAAGGCACC |

TABLE 2-continued

Oligonucleotides used for gene assembly in
this study (SEQ ID NOs: 54-65)

| Primer Name | Oligonucleotide sequence (5' → 3') |
|---|---|
| WK204 | CCTCGTGGCCAACCATGCAAGAGAAAGTGTCGCCCTTCTTC-CAG<br>TCCTCCGCAGCGACCCTCAGGATGCTGGTGACGGC-GAAGGTGGT<br>GGTGCCTTGGCTGGGCTC |
| WK206 | CTTGCATGGTTGGCCACGAGGCCCTGCCCCTGGCCTTCAC-CCAG<br>AAGACCATCGACAGGCACCACCATCATCACCACTGATCTA-GAAG<br>C |
| WK207 | CGAGGCTGATCAGCGAGCTTCTAGATCAGTGGTGATGATG-GTGG<br>TG |

TABLE 3

Plasmids used in this study

| Plasmids | Relevant characteristics | Reference or Source |
|---|---|---|
| pTrc-DsbA IgA CH2 CH3 | IgA Fc domain with truncated tailpiece (Residues 222-445) in bacterial expression vector | This study |
| pMaz-IgH-FcαRI-GST | FcαRI gene in pMaz-IgH for dimeric mammalian expression | This study |
| pMaz-IgH-FcγRI-His | FcγRI gene in pMaz-IgH for monomeric mammalian expression | This study |
| pMaz-IgH-FcγRI-GST | FcγRI gene in pMaz-IgH for dimeric mammalian expression | (Jung et al., 2012) |
| pMaz-IgH-FcγRIIa$_{R131}$-GST | FcγRIIa gene in pMaz-IgH for dimeric mammalian expression | (Jung et al., 2012) |
| pMaz-IgH-FcγRIIb-GST | FcγRIIb gene in pMaz-IgH for dimeric mammalian expression | (Jung et al., 2012) |
| pMaz-IgH-FcγRIIIa-GST | FcγRIIIa gene in pMaz-IgH for dimeric mammalian expression | (Jung et al., 2012) |
| pMaz-IgH-MutB | Mutant B Fc domain only in dimeric mammalian expression vector | This study |
| pMaz-IgH-MutC | Mutant C Fc domain only in dimeric mammalian expression vector | This study |
| pMaz-IgH-MutD | Mutant D Fc domain only in dimeric mammalian expression vector | This study |
| pMaz-IgH-trastuzumab | Wild type IgG1 trastuzumab heavy chain mammalian expression vector | (Jung et al., 2012) |
| pMaz-IgL-trastuzumab | Wild type IgG1 trastuzumab kappa light chain mammalian expression vector | (Jung et al., 2012) |
| pMaz-IgH-IgA-trastuzumab | Wild type IgA1 trastuzumab mammalian expression vector | This study |
| pMaz-IgH-N297D-trastuzumab | IgG1 trastuzumab heavy chain mammalian expression vector with glycosylation knockout at N297 | (Jung et al., 2012) |
| pMaz-IgH-MutD-trastuzumab | Mutant D trastuzumab in a mammalian expression vector | This study |
| pcDNA3.4-FcγRIIb-His | Soluble His tagged monomeric FcγRIIb mammalian expression vector | This study |
| pcDNA3.4-FcγRIIa$_{R131}$-His | Soluble His tagged monomeric FcγRIIa$_{R131}$ mammalian expression vector | This study |

Example 9—Screening for Higher Affinity

Structure-Based Library Design.

At Fc residues found to have the modest influence on interaction with FcαRI and at residues in close proximity to energetically important residues, mutations can be introduced to create combinatorial libraries of mutant D likely to give rise to variants displaying higher affinity to FcαRI. Biased codons can be chosen where possible to reduce the size of the library required to cover the total theoretical diversity. Gene assembly is used to generate a library based on mutant D with a theoretical diversity of about $1 \times 10^8$. Primers specific for the library can be used for amplification and cloning into SfiI-digested pPelBFLAG. The resulting plasmid library was transformed into E. coli Jude-1 (F' [Tn10(Tetr) proAB+ lacIq Δ(lacZ)M15] mcrA Δ(mrr-hs-dRMS-mcrBC) φ80dlacZΔM15 ΔlacX74 deoR recA1 araD139 Δ(ara leu)7697 galU galK rpsL endA1 nupG) and plated on LB agar plates containing chloramphenicol and 2% glucose (w/v).

Error Prone Library Construction.

In addition to the library design guided by alanine scanning mutagenesis, the mutant D gene can be randomly mutated by error prone PCR since there are established instances where mutations located distal to a receptor binding site can have a large influence on the affinity of the interaction (Jung et al., 2010; Jung et al., 2012). Using a standard error prone PCR method (Fromant et al., 1995) and mutant D as a template, a library insert can be generated. The amplified fragment can be SfiI digested and ligated into pPelBFLAG digested in the same manner. The resulting plasmids are then transformed into JUDE-1 cells by electroporation and plated on LB agar plates containing chloramphenicol and 2% glucose (w/v). An error prone library exceeding $1 \times 10^8$ individual variants can be created with an error rate of 0.6% as calculated from the sequencing of 10 randomly chosen variants.

Library Screening—Spheroplast Preparation.

Thawed aliquots of library cells can be cultured for six hours at 37° C. with 250 rpm shaking in Terrific Broth (Becton Dickinson) with 2% (w/v) glucose supplemented with chloramphenicol (50 µg/mL) then diluted 1:50 in fresh TB media containing 0.5 M trehalose (Fisher Scientific) and chloramphenicol (40 µg/mL). After three hours incubation at 37° C. with 250 rpm shaking and a 20 min cooling step at 25° C., the expression of Fc fragments is induced with 1 mM isopropyl-1-thio-β-D-galactopyranoside (IPTG). After culture overnight at 25° C., 8 OD equivalents of the culture broth can be harvested by centrifugation and washed two times in 1 mL of cold 10 mM Tris-HCl (pH 8.0). After resuspension in 1 mL of cold STE solution (0.5 M Sucrose, 10 mM Tris-HCl, 10 mM EDTA, pH 8.0), the cells are incubated with rotating mixing at 37° C. for 30 min, recovered by centrifugation at 12,000×g for 1, and washed in 1 mL of cold Solution A (0.5 M sucrose, 20 mM MgCl$_2$, 10 mM MOPS, pH 6.8). The washed cells are incubated in 1 mL of Solution A containing 1 mg/mL of hen egg lysozyme at 37° C. for 15 min. After centrifugation at 12,000×g for 1 min the resulting spheroplasts pellets were resuspended in 1 mL of cold PBS.

Library Screening—Cell Sorting.

For library screening, the extracellular domain of recombinant expressed FcαRI-GST/CD89 can be fluorescently labeled with an Alexa Fluor 488 labeling kit (Invitrogen, Carlsbad, Calif.). After the labeling reaction, the activity of FcαRI-GST was confirmed using ELISA by determining receptor association with coated human IgA from serum using goat anti-GST HRP for detection. Spheroplasts are labeled with 100 nM of FcαRI-GST-488 in PBS at 4° C. for 1 hour. During the 4th round of sorting, the concentration of FcαRI-GST was reduced to 50 nM and finally to 20 nM in the final round. More than $4\times10^8$ spheroplasted cells can be sorted on an Aria flow cytometer (BD Biosciences) equipped with a 488 nm laser for excitation. In each round the top 3% of the population showing the highest fluorescence due to FcαRIa-GST-488 binding can be isolated and resorted immediately after the initial sorting.

Library Screening—Library Recovery.

After each round of sorting the pool of Fc genes in the spheroplasts can be rescued by PCR amplification using specific primers, ligated into pPelBFLAG on SfiI restriction enzyme sites, and transformed back into electrocompetent E. coli Jude-1 cells. The resulting transformants are plated on agar plates containing chloramphenicol, recovered, and then grown in liquid culture for spheroplasting in subsequent sorting rounds. After five rounds of screening with FcαRI-GST-, a panel of variants with higher fluorescence than mutant D may be isolated.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Woof, J. M., and Kerr, M. A. (2006) The function of immunoglobulin A in immunity, The Journal of Pathology 208, 270-282.

Morell, A., Skvaril, F., Noseda, G., and Brandun, S. (1973) Metabolic properties of human IgA subclasses, Clinical and Experimental Immunology 13, 521.

Jacob, C., Pastorino, A., Fahl, K., Carneiro-Sampaio, M., and Monteiro, R. (2008) Autoimmunity in IgA deficiency: revisiting the role of IgA as a silent housekeeper, Journal of Clinical Immunology 28, 56-61.

Qian, K., Xie, F., Gibson, A., Edberg, J., Kimberly, R., and Wu, J. (2008) Functional expression of IgA receptor Fc {alpha} RI on human platelets, Journal of Leukocyte Biology 84, 1492.

Woof, J., and Kerr, M. (2004) IgA function—variations on a theme, Immunology 113, 175.

van Egmond, M., Damen, C., van Spriel, A., Vidarsson, G., van Garderen, E., and van de Winkel, J. (2001) IgA and the IgA Fc receptor, TRENDS in Immunology 22, 205-211.

Stockmeyer, B., Dechant, M., van Egmond, M., Tutt, A., Sundarapandiyan, K., Graziano, R., Repp, R., Kalden, J., Gramatzki, M., and Glennie, M. (2000) Triggering Fc {alpha}-receptor I (CD89) recruits neutrophils as effector cells for CD20-directed antibody therapy, The Journal of Immunology 165, 5954.

Pasquier, B., Launay, P., Kanamaru, Y., Moura, I., Pfirsch, S., Ruffle, C., Hénin, D., Benhamou, M., Pretolani, M., and Blank, U. (2005) Identification of Fc RI as an Inhibitory Receptor that Controls Inflammation Dual Role of FcR ITAM, Immunity 22, 31-42.

Pleass, R. J., Dunlop, J. I., Anderson, C. M., and Woof, J. M. (1999) Identification of Residues in the CH2/CH3 Domain Interface of IgA Essential for Interaction with the Human Fcα Receptor (FcαR) CD89, Journal of Biological Chemistry 274, 23508-23514.

Herr, A. B., Ballister, E. R., and Bjorkman, P. J. (2003) Insights into IgA-mediated immune responses from the crystal structures of human Fc RI and its complex with IgA1-Fc, Nature 423, 614-620.

Benhar, I., and Mazor, Y. (2008) Recombinant fusion protein and polynucleotide construct for immunotoxin production, Google Patents.

Gibson, D. G., Young, L., Chuang, R. Y., Venter, J. C., Hutchison, C. A., and Smith, H. O. (2009) Enzymatic assembly of DNA molecules up to several hundred kilobases, Nature methods 6, 343-345.

Jung, S., Reddy, S., Kang, T., Borrok, M., Sandlie, I., Tucker, P., and Georgiou, G. (2010) Aglycosylated IgG variants expressed in bacteria that selectively bind Fc RI potentiate tumor cell killing by monocyte-dendritic cells, Proceedings of the National Academy of Sciences 107, 604.

Jung, S. T., Kelton, W., Kang, T. H., Ng, D. T. W., Andersen, J. T., Sandlie, I., Sarkar, C. A., and Georgiou, G. (2012) Effective Phagocytosis of Low Her2 Tumor Cell Lines with Engineered, Aglycosylated IgG Displaying High FcγRIIa Affinity and Selectivity, ACS Chemical Biology.

Fromant, M., Blanquet, S., and Plateau, P. (1995) Direct random mutagenesis of gene-sized DNA fragments using polymerase chain reaction, Analytical Biochemistry 224, 347-353.

Pier, G. B., Kelly-Quintos, C. A., Cavacini, L., and Posner, M. R. (2005) Poly-N-acetyl glucosamine (PNAG/DP-NAG)-binding peptides and methods of use thereof, WO Patent WO/2005/103,084.

Kabat et al., In: *Sequences of Proteins of Immunological Interest*, 5th Ed., Public Health Service, National Institute of Health, Bethesda, Md., 1991.

What is claimed is:

1. A recombinant polypeptide comprising a single immunoglobulin Fc domain, the Fc domain consists of at least 85% sequence identity to the sequence of SEQ ID NO: 8, and wherein the immunoglobulin Fc domain consists of (a) a single chimeric CH2 domain having an α1 loop corresponding to amino acids 245-257 of a human IgA Fc, according to the Kabat numbering scheme, and (b) a single CH3 domain.

2. The polypeptide of claim 1, further comprising an immunoglobulin variable domain.

3. The polypeptide of claim 1, wherein the single chimeric CH2 domain is a CH2γ domain comprising said α1 loop, and/or the CH3 domain is a CH3a domain.

4. The polypeptide of claim 1, wherein the α1 loop domain comprises the sequence PALEDLLLGSEAN (SEQ ID NO: 14).

5. The polypeptide of claim 1, wherein the immunoglobulin Fc domain comprises the sequence PALEDLLLGSEANG (SEQ ID NO: 15).

6. The polypeptide of claim 1, further comprising a FcRn-binding peptide at the C-terminus.

7. The polypeptide of claim 6, wherein the FcRn-binding peptide is the linear peptide of SEQ ID NO: 67 or the cyclic peptide of SEQ ID NO: 68.

8. A recombinant antibody comprising the polypeptide sequence in accordance with claim 1.

9. The antibody of claim 8, wherein the antibody is a human or humanized antibody.

10. The antibody of claim 8, wherein the antibody is aglycosylated.

11. The antibody of claim 8, wherein the antibody binds to a cell surface antigen.

12. The antibody of claim 8, wherein the antibody binds to a cancer cell antigen.

13. The antibody of claim 11, wherein the antibody binds to an EGFR or VEGFR.

14. The antibody of claim 13, wherein the antibody binds to HER2.

15. The antibody of claim 8, wherein the antibody is coupled to a therapeutic, a reporter, or a targeting moiety.

16. The antibody of claim 15, wherein the therapeutic is a nucleotide, a peptide, a small molecule, a therapeutic radionuclide, a chemotherapeutic, a tumor suppressor, an apoptosis inducer, an enzyme, a second antibody, an siRNA, a hormone, a prodrug, or an immunostimulant.

17. The antibody of claim 8, wherein the antibody comprises one or more of the following:
(a) decreased affinity for FcγRIIb relative to a wild type IgG antibody;
(b) increased affinity for FcγRIIa relative to a wild type IgA antibody;
(c) increased affinity for FcγRI relative to a wild type IgA antibody; and
(d) increased affinity for FcαRI relative to a wild type IgG antibody.

18. A composition comprising the recombinant antibody of claim 8 and a buffer, diluent or excipient.

19. The polypeptide of claim 1, wherein the immunoglobulin Fc domain consisting a sequence at least 90% identical to SEQ ID NO: 8.

20. The antibody of claim 8, wherein the antibody is a bispecific antibody.

* * * * *

UNITED STATES PATENT AND TRADEMARK OFFICE
CERTIFICATE OF CORRECTION

PATENT NO. : 9,890,216 B2
APPLICATION NO. : 14/437544
DATED : February 13, 2018
INVENTOR(S) : George Georgiou, William Kelton and Nishant Mehta Page 1 of 1

It is certified that error appears in the above-identified patent and that said Letters Patent is hereby corrected as shown below:

In Claim 3, Column 75, Line 24, delete "CH3a" and insert --CH3α-- therefor.

Signed and Sealed this
Fifteenth Day of May, 2018

Andrei Iancu
*Director of the United States Patent and Trademark Office*

SEQUENCE LISTING

<160> NUMBER OF SEQ ID NOS: 82

<210> SEQ ID NO 1
<211> LENGTH: 227
<212> TYPE: PRT

<213> ORGANISM: Homo sapiens

<400> SEQUENCE: 1

```
Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
            20                  25                  30
Ile Ser Arg Thr Pro Glu Val Thr Cys Val Val Val Asp Val Ser His
        35                  40                  45
Glu Asp Pro Glu Val Lys Phe Asn Trp Tyr Val Asp Gly Val Glu Val
    50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
    130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly Lys
225
```

```
<210> SEQ ID NO 2
<211> LENGTH: 230
<212> TYPE: PRT
<213> ORGANISM: Artificial Sequence
<220> FEATURE:
<223> OTHER INFORMATION: Recombinant Polypeptide
```

<400> SEQUENCE: 2

```
Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
            20                  25                  30
Ile Ser Arg Thr Pro Glu Val Thr Cys Val Val Val Asp Val Ser His
        35                  40                  45
Glu Asp Pro Glu Val Lys Phe Asn Trp Tyr Val Asp Gly Val Glu Val
    50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
```

```
Glu Lys Thr Ile Ser Lys Ala Lys Ser Gly Asn Thr Phe Arg Pro Glu
            115                 120                 125

Val His Leu Leu Pro Pro Ser Glu Glu Leu Ala Leu Asn Glu Leu
    130                 135                 140

Val Thr Leu Thr Cys Leu Ala Arg Gly Phe Ser Pro Lys Asp Val Leu
145                 150                 155                 160

Val Arg Trp Leu Gln Gly Ser Gln Glu Leu Pro Arg Glu Lys Tyr Leu
                165                 170                 175

Thr Trp Ala Ser Arg Gln Glu Pro Ser Gln Gly Thr Thr Thr Phe Ala
                180                 185                 190

Val Thr Ser Ile Leu Arg Val Ala Ala Glu Asp Trp Lys Lys Gly Asp
                195                 200                 205

Thr Phe Ser Cys Met Val Gly His Glu Ala Leu Pro Leu Ala Phe Thr
                210                 215                 220

Gln Lys Thr Ile Asp Arg
225                 230

<210> SEQ ID NO 3
<211> LENGTH: 229
<212> TYPE: PRT
<213> ORGANISM: Artificial Sequence
<220> FEATURE:
<223> OTHER INFORMATION: Recombinant Polypeptide

<400> SEQUENCE: 3

Asp Lys Thr His Thr Cys Pro Pro Cys Pro Ala Pro Glu Leu Leu Gly
1               5                   10                  15

Gly Pro Ser Val Phe Leu Phe Pro Pro Ala Leu Glu Asp Leu Leu Leu
                20                  25                  30

Gly Ser Glu Ala Asn Val Thr Cys Val Val Asp Val Ser His Glu
            35                  40                  45

Asp Pro Glu Val Lys Phe Asn Trp Tyr Val Asp Gly Val Glu Val His
        50                  55                  60

Asn Ala Lys Thr Lys Pro Arg Glu Glu Gln Tyr Asn Ser Thr Tyr Arg
65                  70                  75                  80

Val Val Ser Val Leu Thr Val Leu His Gln Asp Trp Leu Asn Gly Lys
                85                  90                  95

Glu Tyr Lys Cys Lys Val Ser Asn Lys Ala Leu Pro Ala Pro Ile Glu
            100                 105                 110

Lys Thr Ile Ser Lys Ala Lys Ser Gly Asn Thr Phe Arg Pro Glu Val
            115                 120                 125

His Leu Leu Pro Pro Ser Glu Glu Leu Ala Leu Asn Glu Leu Val
    130                 135                 140

Thr Leu Thr Cys Leu Ala Arg Gly Phe Ser Pro Lys Asp Val Leu Val
145                 150                 155                 160

Arg Trp Leu Gln Gly Ser Gln Glu Leu Pro Arg Glu Lys Tyr Leu Thr
                165                 170                 175

Trp Ala Ser Arg Gln Glu Pro Ser Gln Gly Thr Thr Thr Phe Ala Val
                180                 185                 190

Thr Ser Ile Leu Arg Val Ala Ala Glu Asp Trp Lys Lys Gly Asp Thr
                195                 200                 205

Phe Ser Cys Met Val Gly His Glu Ala Leu Pro Leu Ala Phe Thr Gln
                210                 215                 220

Lys Thr Ile Asp Arg
225
```

<210> SEQ ID NO 4
<211> LENGTH: 230
<212> TYPE: PRT
<213> ORGANISM: Artificial Sequence
<220> FEATURE:
<223> OTHER INFORMATION: Recombinant Polypeptide

<400> SEQUENCE: 4

Asp Lys Thr His Thr Cys Pro Pro Cys Pro Ala Pro Glu Leu Leu Gly
1               5                   10                  15

Gly Pro Ser Val Phe Leu Phe Pro Pro Ala Leu Glu Asp Leu Leu Leu
            20                  25                  30

Gly Ser Glu Ala Asn Gly Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Ser Gly Asn Thr Phe Arg Pro Glu
        115                 120                 125

Val His Leu Leu Pro Pro Ser Glu Glu Leu Ala Leu Asn Glu Leu
    130                 135                 140

Val Thr Leu Thr Cys Leu Ala Arg Gly Phe Ser Pro Lys Asp Val Leu
145                 150                 155                 160

Val Arg Trp Leu Gln Gly Ser Gln Glu Leu Pro Arg Glu Lys Tyr Leu
                165                 170                 175

Thr Trp Ala Ser Arg Gln Glu Pro Ser Gln Gly Thr Thr Thr Phe Ala
            180                 185                 190

Val Thr Ser Ile Leu Arg Val Ala Ala Glu Asp Trp Lys Lys Gly Asp
        195                 200                 205

Thr Phe Ser Cys Met Val Gly His Glu Ala Leu Pro Leu Ala Phe Thr
    210                 215                 220

Gln Lys Thr Ile Asp Arg
225                 230

<210> SEQ ID NO 5
<211> LENGTH: 218
<212> TYPE: PRT
<213> ORGANISM: Homo sapiens

<400> SEQUENCE: 5

Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Lys Phe Asn Trp
        35                  40                  45

Tyr Val Asp Gly Val Glu Val His Asn Ala Lys Thr Lys Pro Arg Glu
    50                  55                  60

Glu Gln Tyr Asn Ser Thr Tyr Arg Val Val Ser Val Leu Thr Val Leu
65                  70                  75                  80

```
His Gln Asp Trp Leu Asn Gly Lys Glu Tyr Lys Cys Lys Val Ser Asn
                85                  90                  95

Lys Ala Leu Pro Ala Pro Ile Glu Lys Thr Ile Ser Lys Ala Lys Gly
            100                 105                 110

Gln Pro Arg Glu Pro Gln Val Tyr Thr Leu Pro Pro Ser Arg Asp Glu
        115                 120                 125

Leu Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly Lys
    210                 215

<210> SEQ ID NO 6
<211> LENGTH: 221
<212> TYPE: PRT
<213> ORGANISM: Artificial Sequence
<220> FEATURE:
<223> OTHER INFORMATION: Recombinant polypeptide

<400> SEQUENCE: 6

Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Lys Phe Asn Trp
        35                  40                  45

Tyr Val Asp Gly Val Glu Val His Asn Ala Lys Thr Lys Pro Arg Glu
    50                  55                  60

Glu Gln Tyr Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Ala Leu Pro Ala Pro Ile Glu Lys Thr Ile Ser Lys Ala Lys Ser
            100                 105                 110

Gly Asn Thr Phe Arg Pro Glu Val His Leu Leu Pro Pro Ser Glu
        115                 120                 125

Glu Leu Ala Leu Asn Glu Leu Val Thr Leu Thr Cys Leu Ala Arg Gly
    130                 135                 140

Phe Ser Pro Lys Asp Val Leu Val Arg Trp Leu Gln Gly Ser Gln Glu
145                 150                 155                 160

Leu Pro Arg Glu Lys Tyr Leu Thr Trp Ala Ser Arg Gln Glu Pro Ser
                165                 170                 175

Gln Gly Thr Thr Thr Phe Ala Val Thr Ser Ile Leu Arg Val Ala Ala
            180                 185                 190

Glu Asp Trp Lys Lys Gly Asp Thr Phe Ser Cys Met Val Gly His Glu
        195                 200                 205

Ala Leu Pro Leu Ala Phe Thr Gln Lys Thr Ile Asp Arg
    210                 215                 220
```

```
<210> SEQ ID NO 7
<211> LENGTH: 220
<212> TYPE: PRT
<213> ORGANISM: Artificial Sequence
<220> FEATURE:
<223> OTHER INFORMATION: Recombinant polypeptide

<400> SEQUENCE: 7

Pro Ala Pro Glu Leu Leu Gly Gly Pro Ser Val Phe Leu Phe Pro Pro
1               5                   10                  15

Ala Leu Glu Asp Leu Leu Leu Gly Ser Glu Ala Asn Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Ser Gly
            100                 105                 110

Asn Thr Phe Arg Pro Glu Val His Leu Leu Pro Pro Ser Glu Glu
        115                 120                 125

Leu Ala Leu Asn Glu Leu Val Thr Leu Thr Cys Leu Ala Arg Gly Phe
    130                 135                 140

Ser Pro Lys Asp Val Leu Val Arg Trp Leu Gln Gly Ser Gln Glu Leu
145                 150                 155                 160

Pro Arg Glu Lys Tyr Leu Thr Trp Ala Ser Arg Gln Glu Pro Ser Gln
                165                 170                 175

Gly Thr Thr Thr Phe Ala Val Thr Ser Ile Leu Arg Val Ala Ala Glu
            180                 185                 190

Asp Trp Lys Lys Gly Asp Thr Phe Ser Cys Met Val Gly His Glu Ala
        195                 200                 205

Leu Pro Leu Ala Phe Thr Gln Lys Thr Ile Asp Arg
    210                 215                 220

<210> SEQ ID NO 8
<211> LENGTH: 221
<212> TYPE: PRT
<213> ORGANISM: Artificial Sequence
<220> FEATURE:
<223> OTHER INFORMATION: Recombinant polypeptide

<400> SEQUENCE: 8

Pro Ala Pro Glu Leu Leu Gly Gly Pro Ser Val Phe Leu Phe Pro Pro
1               5                   10                  15

Ala Leu Glu Asp Leu Leu Leu Gly Ser Glu Ala Asn Gly Val Thr Cys
            20                  25                  30

Val Val Val Asp Val Ser His Glu Asp Pro Glu Val Lys Phe Asn Trp
        35                  40                  45

Tyr Val Asp Gly Val Glu Val His Asn Ala Lys Thr Lys Pro Arg Glu
    50                  55                  60

Glu Gln Tyr Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95
```

Lys Ala Leu Pro Ala Pro Ile Glu Lys Thr Ile Ser Lys Ala Lys Ser
            100                 105                 110

Gly Asn Thr Phe Arg Pro Glu Val His Leu Leu Pro Pro Ser Glu
            115                 120                 125

Glu Leu Ala Leu Asn Glu Leu Val Thr Leu Thr Cys Leu Ala Arg Gly
130                 135                 140

Phe Ser Pro Lys Asp Val Leu Val Arg Trp Leu Gln Gly Ser Gln Glu
145                 150                 155                 160

Leu Pro Arg Glu Lys Tyr Leu Thr Trp Ala Ser Arg Gln Glu Pro Ser
                165                 170                 175

Gln Gly Thr Thr Thr Phe Ala Val Thr Ser Ile Leu Arg Val Ala Ala
            180                 185                 190

Glu Asp Trp Lys Lys Gly Asp Thr Phe Ser Cys Met Val Gly His Glu
            195                 200                 205

Ala Leu Pro Leu Ala Phe Thr Gln Lys Thr Ile Asp Arg
    210                 215                 220

<210> SEQ ID NO 9
<211> LENGTH: 110
<212> TYPE: PRT
<213> ORGANISM: Homo sapiens

<400> SEQUENCE: 9

Ser Gly Asn Thr Phe Arg Pro Glu Val His Leu Leu Pro Pro Ser
1               5                   10                  15

Glu Glu Leu Ala Leu Asn Glu Leu Val Thr Leu Thr Cys Leu Ala Arg
            20                  25                  30

Gly Phe Ser Pro Lys Asp Val Leu Val Arg Trp Leu Gln Gly Ser Gln
        35                  40                  45

Glu Leu Pro Arg Glu Lys Tyr Leu Thr Trp Ala Ser Arg Gln Glu Pro
    50                  55                  60

Ser Gln Gly Thr Thr Thr Phe Ala Val Thr Ser Ile Leu Arg Val Ala
65                  70                  75                  80

Ala Glu Asp Trp Lys Lys Gly Asp Thr Phe Ser Cys Met Val Gly His
                85                  90                  95

Glu Ala Leu Pro Leu Ala Phe Thr Gln Lys Thr Ile Asp Arg
            100                 105                 110

<210> SEQ ID NO 10
<211> LENGTH: 108
<212> TYPE: PRT
<213> ORGANISM: Homo sapiens

<400> SEQUENCE: 10

Lys Gly Gln Pro Arg Glu Pro Gln Val Tyr Thr Leu Pro Pro Ser Arg
1               5                   10                  15

Asp Glu Leu Thr Lys Asn Gln Val Ser Leu Thr Cys Leu Val Lys Gly
            20                  25                  30

Phe Tyr Pro Ser Asp Ile Ala Val Glu Trp Glu Ser Asn Gly Gln Pro
        35                  40                  45

Glu Asn Asn Tyr Lys Thr Thr Pro Pro Val Leu Asp Ser Asp Gly Ser
    50                  55                  60

Phe Phe Leu Tyr Ser Lys Leu Thr Val Asp Lys Ser Arg Trp Gln Gln
65                  70                  75                  80

Gly Asn Val Phe Ser Cys Ser Val Met His Glu Ala Leu His Asn His
                85                  90                  95

Tyr Thr Gln Lys Ser Leu Ser Leu Ser Pro Gly Lys
            100                 105

<210> SEQ ID NO 11
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 11

Asp Lys Thr His Thr Cys Pro Pro Cys Pro Ala Pro Glu Leu Leu Gly
1               5                   10                  15

Gly Pro Ser Val Phe Leu Phe Pro Pro Ala Leu Glu Asp Leu Leu Leu
            20                  25                  30

Gly Ser Glu Ala Asn Val Thr Cys Val Val Val Asp Val Ser His Glu
        35                  40                  45

Asp Pro Glu Val Lys Phe Asn Trp Tyr Val Asp Gly Val Glu Val His
    50                  55                  60

Asn Ala Lys Thr Lys Pro Arg Glu Glu Gln Tyr Asn Ser Thr Tyr Arg
65                  70                  75                  80

Val Val Ser Val Leu Thr Val Leu His Gln Asp Trp Leu Asn Gly Lys
                85                  90                  95

Glu Tyr Lys Cys Lys Val Ser Asn Lys Ala Leu Pro Ala Pro Ile Glu
            100                 105                 110

Lys Thr Ile Ser Lys Ala Lys
        115

<210> SEQ ID NO 12
<211> LENGTH: 120
<212> TYPE: PRT
<213> ORGANISM: Artificial Sequence
<220> FEATURE:
<223> OTHER INFORMATION: Synthetic polypeptide

<400> SEQUENCE: 12

Asp Lys Thr His Thr Cys Pro Pro Cys Pro Ala Pro Glu Leu Leu Gly
1               5                   10                  15

Gly Pro Ser Val Phe Leu Phe Pro Pro Ala Leu Glu Asp Leu Leu Leu
            20                  25                  30

Gly Ser Glu Ala Asn Gly Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys
        115                 120

<210> SEQ ID NO 13
<211> LENGTH: 233
<212> TYPE: PRT
<213> ORGANISM: Homo sapiens

<400> SEQUENCE: 13

```
Val Pro Cys Pro Val Pro Ser Thr Pro Pro Thr Pro Ser Pro Ser Thr
1               5                   10                  15

Pro Pro Thr Pro Ser Pro Ser Cys Cys His Pro Arg Leu Ser Leu His
            20                  25                  30

Arg Pro Ala Leu Glu Asp Leu Leu Leu Gly Ser Glu Ala Asn Leu Thr
            35                  40                  45

Cys Thr Leu Thr Gly Leu Arg Asp Ala Ser Gly Val Thr Phe Thr Trp
50                  55                  60

Thr Pro Ser Ser Gly Lys Ser Ala Val Gln Gly Pro Pro Glu Arg Asp
65                  70                  75                  80

Leu Cys Gly Cys Tyr Ser Val Ser Val Leu Pro Gly Cys Ala Glu
                85                  90                  95

Pro Trp Asn His Gly Lys Thr Phe Thr Cys Thr Ala Ala Tyr Pro Glu
                100                 105                 110

Ser Lys Thr Pro Leu Thr Ala Thr Leu Ser Lys Ser Gly Asn Thr Phe
            115                 120                 125

Arg Pro Glu Val His Leu Leu Pro Pro Pro Ser Glu Glu Leu Ala Leu
            130                 135                 140

Asn Glu Leu Val Thr Leu Thr Cys Leu Ala Arg Gly Phe Ser Pro Lys
145                 150                 155                 160

Asp Val Leu Val Arg Trp Leu Gln Gly Ser Gln Glu Leu Pro Arg Glu
                165                 170                 175

Lys Tyr Leu Thr Trp Ala Ser Arg Gln Glu Pro Ser Gln Gly Thr Thr
            180                 185                 190

Thr Phe Ala Val Thr Ser Ile Leu Arg Val Ala Ala Glu Asp Trp Lys
            195                 200                 205

Lys Gly Asp Thr Phe Ser Cys Met Val Gly His Glu Ala Leu Pro Leu
            210                 215                 220

Ala Phe Thr Gln Lys Thr Ile Asp Arg
225                 230

<210> SEQ ID NO 14
<211> LENGTH: 13
<212> TYPE: PRT
<213> ORGANISM: Homo sapiens

<400> SEQUENCE: 14

Pro Ala Leu Glu Asp Leu Leu Leu Gly Ser Glu Ala Asn
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Synthetic peptide

<400> SEQUENCE: 15

Pro Ala Leu Glu Asp Leu Leu Leu Gly Ser Glu Ala Asn Gly
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 16
```

```
Pro Lys Pro Lys Asp Thr Leu Met Ile Ser Arg Thr Pro Glu
1               5                   10
```

<210> SEQ ID NO 17
<211> LENGTH: 33
<212> TYPE: DNA
<213> ORGANISM: Artificial Sequence
<220> FEATURE:
<223> OTHER INFORMATION: Synthetic primer

<400> SEQUENCE: 17
gcgttggaag accttgcgct tggtagcgaa gcg        33

<210> SEQ ID NO 18
<211> LENGTH: 33
<212> TYPE: DNA
<213> ORGANISM: Artificial Sequence
<220> FEATURE:
<223> OTHER INFORMATION: Synthetic primer

<400> SEQUENCE: 18
cgcttcgcta ccaagcgcaa ggtcttccaa cgc        33

<210> SEQ ID NO 19
<211> LENGTH: 38
<212> TYPE: DNA
<213> ORGANISM: Artificial Sequence
<220> FEATURE:
<223> OTHER INFORMATION: Synthetic primer

<400> SEQUENCE: 19
cgttggaaga ccttctggcg ggtagcgaag cgaatctg        38

<210> SEQ ID NO 20
<211> LENGTH: 38
<212> TYPE: DNA
<213> ORGANISM: Artificial Sequence
<220> FEATURE:
<223> OTHER INFORMATION: Synthetic primer

<400> SEQUENCE: 20
cagattcgct tcgctacccg ccagaaggtc ttccaacg        38

<210> SEQ ID NO 21
<211> LENGTH: 33
<212> TYPE: DNA
<213> ORGANISM: Artificial Sequence
<220> FEATURE:
<223> OTHER INFORMATION: Synthetic primer

<400> SEQUENCE: 21
ctgtcgggtt gcgcagcgcc gtggaatcat ggc        33

<210> SEQ ID NO 22
<211> LENGTH: 33
<212> TYPE: DNA
<213> ORGANISM: Artificial Sequence
<220> FEATURE:
<223> OTHER INFORMATION: Synthetic primer

<400> SEQUENCE: 22
gccatgattc cacggcgctg cgcaacccga cag        33

<210> SEQ ID NO 23
<211> LENGTH: 38

-continued

<210> SEQ ID NO 23
<211> LENGTH: 38
<212> TYPE: DNA
<213> ORGANISM: Artificial Sequence
<220> FEATURE:
<223> OTHER INFORMATION: Synthetic primer

<400> SEQUENCE: 23
ggttgcgcag aaccgtgggc gcatggcaaa acattcac                               38

<210> SEQ ID NO 24
<211> LENGTH: 38
<212> TYPE: DNA
<213> ORGANISM: Artificial Sequence
<220> FEATURE:
<223> OTHER INFORMATION: Synthetic primer

<400> SEQUENCE: 24
gtgaatgttt tgccatgcgc ccacggttct gcgcaacc                               38

<210> SEQ ID NO 25
<211> LENGTH: 37
<212> TYPE: DNA
<213> ORGANISM: Artificial Sequence
<220> FEATURE:
<223> OTHER INFORMATION: Synthetic primer

<400> SEQUENCE: 25
gcgcagaacc gtggaatgcg ggcaaaacat tcacctg                                37

<210> SEQ ID NO 26
<211> LENGTH: 37
<212> TYPE: DNA
<213> ORGANISM: Artificial Sequence
<220> FEATURE:
<223> OTHER INFORMATION: Synthetic primer

<400> SEQUENCE: 26
caggtgaatg ttttgcccgc attccacggt tctgcgc                                37

<210> SEQ ID NO 27
<211> LENGTH: 36
<212> TYPE: DNA
<213> ORGANISM: Artificial Sequence
<220> FEATURE:
<223> OTHER INFORMATION: Synthetic primer

<400> SEQUENCE: 27
cgaaagatgt tctggtggcg tggctgcagg gaagcc                                 36

<210> SEQ ID NO 28
<211> LENGTH: 36
<212> TYPE: DNA
<213> ORGANISM: Artificial Sequence
<220> FEATURE:
<223> OTHER INFORMATION: Synthetic primer

<400> SEQUENCE: 28
ggcttccctg cagccacgcc accagaacat ctttcg                                 36

<210> SEQ ID NO 29
<211> LENGTH: 32
<212> TYPE: DNA
<213> ORGANISM: Artificial Sequence
<220> FEATURE:
<223> OTHER INFORMATION: Synthetic primer

<400> SEQUENCE: 29
tgcagggaag ccaagcgctg ccccgtgaaa ag          32

<210> SEQ ID NO 30
<211> LENGTH: 32
<212> TYPE: DNA
<213> ORGANISM: Artificial Sequence
<220> FEATURE:
<223> OTHER INFORMATION: Synthetic primer

<400> SEQUENCE: 30
cttttcacgg ggcagcgctt ggcttccctg ca          32

<210> SEQ ID NO 31
<211> LENGTH: 32
<212> TYPE: DNA
<213> ORGANISM: Artificial Sequence
<220> FEATURE:
<223> OTHER INFORMATION: Synthetic primer

<400> SEQUENCE: 31
gatacgttca gctgcgcggt gggccatgag gc          32

<210> SEQ ID NO 32
<211> LENGTH: 32
<212> TYPE: DNA
<213> ORGANISM: Artificial Sequence
<220> FEATURE:
<223> OTHER INFORMATION: Synthetic primer

<400> SEQUENCE: 32
gcctcatggc ccaccgcgca gctgaacgta tc          32

<210> SEQ ID NO 33
<211> LENGTH: 27
<212> TYPE: DNA
<213> ORGANISM: Artificial Sequence
<220> FEATURE:
<223> OTHER INFORMATION: Synthetic primer

<400> SEQUENCE: 33
atggtgggcc atgcggcact tccgctg          27

<210> SEQ ID NO 34
<211> LENGTH: 27
<212> TYPE: DNA
<213> ORGANISM: Artificial Sequence
<220> FEATURE:
<223> OTHER INFORMATION: Synthetic primer

<400> SEQUENCE: 34
cagcggaagt gccgcatggc ccaccat          27

<210> SEQ ID NO 35
<211> LENGTH: 37
<212> TYPE: DNA
<213> ORGANISM: Artificial Sequence
<220> FEATURE:
<223> OTHER INFORMATION: Synthetic primer

<400> SEQUENCE: 35
gccatgaggc acttccggcg gcctttactc aaaaaac          37

<210> SEQ ID NO 36
<211> LENGTH: 37
<212> TYPE: DNA
<213> ORGANISM: Artificial Sequence

```
<220> FEATURE:
<223> OTHER INFORMATION: Synthetic primer

<400> SEQUENCE: 36
gttttttgag taaaggccgc cggaagtgcc tcatggc                              37

<210> SEQ ID NO 37
<211> LENGTH: 40
<212> TYPE: DNA
<213> ORGANISM: Artificial Sequence
<220> FEATURE:
<223> OTHER INFORMATION: Synthetic primer

<400> SEQUENCE: 37
gaggcacttc cgctggccgc gactcaaaaa actattgatc                           40

<210> SEQ ID NO 38
<211> LENGTH: 40
<212> TYPE: DNA
<213> ORGANISM: Artificial Sequence
<220> FEATURE:
<223> OTHER INFORMATION: Synthetic primer

<400> SEQUENCE: 38
gatcaatagt tttttgagtc gcggccagcg gaagtgcctc                           40

<210> SEQ ID NO 39
<211> LENGTH: 19
<212> TYPE: DNA
<213> ORGANISM: Artificial Sequence
<220> FEATURE:
<223> OTHER INFORMATION: Synthetic primer

<400> SEQUENCE: 39
cgaggctgat cagcgagct                                                  19

<210> SEQ ID NO 40
<211> LENGTH: 18
<212> TYPE: DNA
<213> ORGANISM: Artificial Sequence
<220> FEATURE:
<223> OTHER INFORMATION: Synthetic primer

<400> SEQUENCE: 40
tgagcggccg ctcgaggc                                                   18

<210> SEQ ID NO 41
<211> LENGTH: 36
<212> TYPE: DNA
<213> ORGANISM: Artificial Sequence
<220> FEATURE:
<223> OTHER INFORMATION: Synthetic primer

<400> SEQUENCE: 41
tttgcccgcc agcctgtcga tggtcttctg ggtgaa                               36

<210> SEQ ID NO 42
<211> LENGTH: 62
<212> TYPE: DNA
<213> ORGANISM: Artificial Sequence
<220> FEATURE:
<223> OTHER INFORMATION: Synthetic primer

<400> SEQUENCE: 42
cgacaggctg gcgggcaaag gcggcggcgg cagccagaga ttctgcaccg gccacttcgg     60
```

<210> SEQ ID NO 43
<211> LENGTH: 27
<212> TYPE: DNA
<213> ORGANISM: Artificial Sequence
<220> FEATURE:
<223> OTHER INFORMATION: Synthetic primer

<400> SEQUENCE: 43
tgatctagaa gctcgctgat cagcctc                                        27

<210> SEQ ID NO 44
<211> LENGTH: 43
<212> TYPE: DNA
<213> ORGANISM: Artificial Sequence
<220> FEATURE:
<223> OTHER INFORMATION: Synthetic primer

<400> SEQUENCE: 44
gcctttctct ccacaggcgc gcactccgtg ccgagcaccc ccc                      43

<210> SEQ ID NO 45
<211> LENGTH: 53
<212> TYPE: DNA
<213> ORGANISM: Artificial Sequence
<220> FEATURE:
<223> OTHER INFORMATION: Synthetic primer

<400> SEQUENCE: 45
cgaggctgat cagcgagctt ctagatcagt gatggtgatg atggtgtttg ccc           53

<210> SEQ ID NO 46
<211> LENGTH: 40
<212> TYPE: DNA
<213> ORGANISM: Artificial Sequence
<220> FEATURE:
<223> OTHER INFORMATION: Synthetic primer

<400> SEQUENCE: 46
ggacaatggt caccgtctcc tcagcgagcc cgacgtctcc                          40

<210> SEQ ID NO 47
<211> LENGTH: 79
<212> TYPE: DNA
<213> ORGANISM: Artificial Sequence
<220> FEATURE:
<223> OTHER INFORMATION: Synthetic primer

<400> SEQUENCE: 47
agatcatttg gctgatcagc gagcttctag atcatttgcc cgccagacga tcaatagttt    60
tttgagtaaa ggccagcgg                                                 79

<210> SEQ ID NO 48
<211> LENGTH: 57
<212> TYPE: DNA
<213> ORGANISM: Artificial Sequence
<220> FEATURE:
<223> OTHER INFORMATION: Synthetic primer

<400> SEQUENCE: 48
gcctcgagcg gccgctcagc cgttgcaggg gtgcaggccg ccgaagtggc cggtgca       57

<210> SEQ ID NO 49
<211> LENGTH: 62

<212> TYPE: DNA
<213> ORGANISM: Artificial Sequence
<220> FEATURE:
<223> OTHER INFORMATION: Synthetic primer

<400> SEQUENCE: 49
cgacaggctg gcgggcaaag gcggcggcgg cagccagaga ttcgtgaccg gccacttcgg    60
cg                                                                  62

<210> SEQ ID NO 50
<211> LENGTH: 84
<212> TYPE: DNA
<213> ORGANISM: Artificial Sequence
<220> FEATURE:
<223> OTHER INFORMATION: Synthetic primer

<400> SEQUENCE: 50
accgtcagtc ttcctcttcc cccccgcgtt ggaagacctt ctgcttggta gcgaagcgaa    60
tggcgtcaca tgcgtggtgg tgga                                          84

<210> SEQ ID NO 51
<211> LENGTH: 57
<212> TYPE: DNA
<213> ORGANISM: Artificial Sequence
<220> FEATURE:
<223> OTHER INFORMATION: Synthetic primer

<400> SEQUENCE: 51
gcctcgagcg gccgctcagc cgttggcggg gtacaggccg ccgaagtggc cggtcac       57

<210> SEQ ID NO 52
<211> LENGTH: 47
<212> TYPE: DNA
<213> ORGANISM: Artificial Sequence
<220> FEATURE:
<223> OTHER INFORMATION: Synthetic primer

<400> SEQUENCE: 52
cccatcgaga aaccatctc caaagccagc ggcaacacct tcagacc                   47

<210> SEQ ID NO 53
<211> LENGTH: 39
<212> TYPE: DNA
<213> ORGANISM: Artificial Sequence
<220> FEATURE:
<223> OTHER INFORMATION: Synthetic primer

<400> SEQUENCE: 53
tcagtcttcc tcttcccccc agccctggag gacttgctg                           39

<210> SEQ ID NO 54
<211> LENGTH: 94
<212> TYPE: DNA
<213> ORGANISM: Artificial Sequence
<220> FEATURE:
<223> OTHER INFORMATION: Synthetic primer

<400> SEQUENCE: 54
tttctctcca caggcgcgca ctccgacaaa actcacacat gcccaccgtg cccagcacct    60
gaactcctgg ggggaccgtc agtcttcctc ttcc                               94

<210> SEQ ID NO 55
<211> LENGTH: 104
<212> TYPE: DNA

<213> ORGANISM: Artificial Sequence
<220> FEATURE:
<223> OTHER INFORMATION: Synthetic primer

<400> SEQUENCE: 55

```
ggtcttcgtg gctcacgtcc accaccacgc atgtgacctc aggggtccgg gagatcatga    60
gggtgtcctt gggttttggg gggaagagga agactgacgg tccc                    104
```

<210> SEQ ID NO 56
<211> LENGTH: 101
<212> TYPE: DNA
<213> ORGANISM: Artificial Sequence
<220> FEATURE:
<223> OTHER INFORMATION: Synthetic primer

<400> SEQUENCE: 56

```
ggtcttcgtg gctcacgtcc accaccacgc acgtcacgtt ggcctcgctg cccagcagca    60
agtcctccag ggctgggggg aagaggaaga ctgacggtcc c                       101
```

<210> SEQ ID NO 57
<211> LENGTH: 104
<212> TYPE: DNA
<213> ORGANISM: Artificial Sequence
<220> FEATURE:
<223> OTHER INFORMATION: Synthetic primer

<400> SEQUENCE: 57

```
ggtcttcgtg gctcacgtcc accaccacgc acgtcacgcc gttggcctcg ctgcccagca    60
gcaagtcctc cagggctggg gggaagagga agactgacgg tccc                    104
```

<210> SEQ ID NO 58
<211> LENGTH: 99
<212> TYPE: DNA
<213> ORGANISM: Artificial Sequence
<220> FEATURE:
<223> OTHER INFORMATION: Synthetic primer

<400> SEQUENCE: 58

```
gtggacgtga gccacgaaga ccctgaggtc aagttcaact ggtacgtgga cggcgtggag    60
gtgcataatg ccaagacaaa gccgcgggag gagcagtac                           99
```

<210> SEQ ID NO 59
<211> LENGTH: 102
<212> TYPE: DNA
<213> ORGANISM: Artificial Sequence
<220> FEATURE:
<223> OTHER INFORMATION: Synthetic primer

<400> SEQUENCE: 59

```
ggagaccttg cacttgtact ccttgccatt cagccagtcc tgtgcagga cggtgaggac     60 gctgaccaca cggtacgtgc tgttgtactg ctcctcccgc gg                      102
```

<210> SEQ ID NO 60
<211> LENGTH: 105
<212> TYPE: DNA
<213> ORGANISM: Artificial Sequence
<220> FEATURE:
<223> OTHER INFORMATION: Synthetic primer

<400> SEQUENCE: 60

```
gcaaggagta caagtgcaag gtctccaaca aagccctccc agccccatc gagaaaacca     60 tctccaaagc cagcggcaac accttcagac ccgaggtgca tctgc                   105
```

<210> SEQ ID NO 61
<211> LENGTH: 107
<212> TYPE: DNA
<213> ORGANISM: Artificial Sequence
<220> FEATURE:
<223> OTHER INFORMATION: Synthetic primer

<400> SEQUENCE: 61
gcacgtcctt ggggctgaag cccctcgcaa ggcaggtgag agtgaccagc tcgttcaggg    60
cgagctcctc gctgggaggg ggcagcagat gcacctcggg tctgaag                 107

<210> SEQ ID NO 62
<211> LENGTH: 106
<212> TYPE: DNA
<213> ORGANISM: Artificial Sequence
<220> FEATURE:
<223> OTHER INFORMATION: Synthetic primer

<400> SEQUENCE: 62
cttcagcccc aaggacgtgc tcgtgaggtg gctgcagggc tcccaggagc tgcccaggga    60
gaagtacctg acctgggcca gcaggcagga gcccagccaa ggcacc                  106

<210> SEQ ID NO 63
<211> LENGTH: 106
<212> TYPE: DNA
<213> ORGANISM: Artificial Sequence
<220> FEATURE:
<223> OTHER INFORMATION: Synthetic primer

<400> SEQUENCE: 63
cctcgtggcc aaccatgcaa gagaaagtgt cgcccttctt ccagtcctcc gcagcgaccc    60
tcaggatgct ggtgacggcg aaggtggtgg tgccttggct gggctc                  106

<210> SEQ ID NO 64
<211> LENGTH: 89
<212> TYPE: DNA
<213> ORGANISM: Artificial Sequence
<220> FEATURE:
<223> OTHER INFORMATION: Synthetic primer

<400> SEQUENCE: 64
cttgcatggt tggccacgag gccctgcccc tggccttcac ccagaagacc atcgacaggc    60
accaccatca tcaccactga tctagaagc                                      89

<210> SEQ ID NO 65
<211> LENGTH: 46
<212> TYPE: DNA
<213> ORGANISM: Artificial Sequence
<220> FEATURE:
<223> OTHER INFORMATION: Synthetic primer

<400> SEQUENCE: 65
cgaggctgat cagcgagctt ctagatcagt ggtgatgatg gtggtg                   46

<210> SEQ ID NO 66
<211> LENGTH: 13
<212> TYPE: PRT
<213> ORGANISM: Homo sapiens

<400> SEQUENCE: 66

Pro Ala Leu Glu Asp Leu Leu Leu Gly Ser Glu Ala Asn
1               5                   10

```
<210> SEQ ID NO 67
<211> LENGTH: 16
<212> TYPE: PRT
<213> ORGANISM: Artificial Sequence
<220> FEATURE:
<223> OTHER INFORMATION: Synthetic pepetide

<400> SEQUENCE: 67

Gln Arg Phe Val Thr Gly His Phe Gly Gly Leu Tyr Pro Ala Asn Gly
1               5                   10                  15

<210> SEQ ID NO 68
<211> LENGTH: 16
<212> TYPE: PRT
<213> ORGANISM: Artificial Sequence
<220> FEATURE:
<223> OTHER INFORMATION: Synthetic pepetide

<400> SEQUENCE: 68

Gln Arg Phe Cys Thr Gly His Phe Gly Gly Leu His Pro Cys Asn Gly
1               5                   10                  15

<210> SEQ ID NO 69
<211> LENGTH: 16
<212> TYPE: DNA
<213> ORGANISM: Artificial Sequence
<220> FEATURE:
<223> OTHER INFORMATION: Synthetic primer

<400> SEQUENCE: 69
tgagcggccg ctcgag                                                     16

<210> SEQ ID NO 70
<211> LENGTH: 24
<212> TYPE: DNA
<213> ORGANISM: Artificial Sequence
<220> FEATURE:
<223> OTHER INFORMATION: Synthetic primer

<400> SEQUENCE: 70
acactggaca cctttgagca cagc                                            24

<210> SEQ ID NO 71
<211> LENGTH: 47
<212> TYPE: DNA
<213> ORGANISM: Artificial Sequence
<220> FEATURE:
<223> OTHER INFORMATION: Synthetic primer

<400> SEQUENCE: 71
cgctgtgctc aaaggtgtcc agtgtcaagc tgctccccca aaggctg                   47

<210> SEQ ID NO 72
<211> LENGTH: 47
<212> TYPE: DNA
<213> ORGANISM: Artificial Sequence
<220> FEATURE:
<223> OTHER INFORMATION: Synthetic primer

<400> SEQUENCE: 72
cgctgtgctc aaaggtgtcc agtgtacacc tgcagctccc ccaaagg                   47

<210> SEQ ID NO 73
<211> LENGTH: 40
<212> TYPE: DNA
```

<213> ORGANISM: Artificial Sequence
<220> FEATURE:
<223> OTHER INFORMATION: Synthetic primer

<400> SEQUENCE: 73
gtggtgatgg tgatgatgcc ccattggtga agagctgccc					40

<210> SEQ ID NO 74
<211> LENGTH: 42
<212> TYPE: DNA
<213> ORGANISM: Artificial Sequence
<220> FEATURE:
<223> OTHER INFORMATION: Synthetic primer

<400> SEQUENCE: 74
gtggtgatgg tgatgatggg gagcttggac agtgatggtc ac					42

<210> SEQ ID NO 75
<211> LENGTH: 26
<212> TYPE: DNA
<213> ORGANISM: Artificial Sequence
<220> FEATURE:
<223> OTHER INFORMATION: Synthetic primer

<400> SEQUENCE: 75
cgccttatcc ggtaactatc gtcttg					26

<210> SEQ ID NO 76
<211> LENGTH: 26
<212> TYPE: DNA
<213> ORGANISM: Artificial Sequence
<220> FEATURE:
<223> OTHER INFORMATION: Synthetic primer

<400> SEQUENCE: 76
gactcaagac gatagttacc ggataa					26

<210> SEQ ID NO 77
<211> LENGTH: 353
<212> TYPE: PRT
<213> ORGANISM: Homo sapiens

<400> SEQUENCE: 77

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
        115                 120                 125

Leu His Arg Pro Ala Leu Glu Asp Leu Leu Leu Gly Ser Glu Ala Asn
    130                 135                 140

```
Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175

Arg Asp Leu Cys Gly Cys Tyr Ser Val Ser Ser Val Leu Pro Gly Cys
            180                 185                 190

Ala Glu Pro Trp Asn His Gly Lys Thr Phe Thr Cys Thr Ala Ala Tyr
        195                 200                 205

Pro Glu Ser Lys Thr Pro Leu Thr Ala Thr Leu Ser Lys Ser Gly Asn
    210                 215                 220

Thr Phe Arg Pro Glu Val His Leu Leu Pro Pro Ser Glu Glu Leu
225                 230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
        275                 280                 285

Thr Thr Thr Phe Ala Val Thr Ser Ile Leu Arg Val Ala Ala Glu Asp
    290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
            340                 345                 350

Tyr

<210> SEQ ID NO 78
<211> LENGTH: 340
<212> TYPE: PRT
<213> ORGANISM: Homo sapiens

<400> SEQUENCE: 78

Ala Ser Pro Thr Ser Pro Lys Val Phe Pro Leu Ser Leu Asp Ser Thr
1               5                   10                  15

Pro Gln Asp Gly Asn Val Val Ala Cys Leu Val Gln Gly Phe Phe
        20                  25                  30

Pro Gln Glu Pro Leu Ser Val Thr Trp Ser Glu Ser Gly Gln Asn Val
            35                  40                  45

Thr Ala Arg Asn Phe Pro Pro Ser Gln Asp Ala Ser Gly Asp Leu Tyr
        50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Pro Pro Pro Cys Cys His Pro
            100                 105                 110

Arg Leu Ser Leu His Arg Pro Ala Leu Glu Asp Leu Leu Leu Gly Ser
        115                 120                 125

Glu Ala Asn Leu Thr Cys Thr Leu Thr Gly Leu Arg Asp Ala Ser Gly
    130                 135                 140

Ala Thr Phe Thr Trp Thr Pro Ser Ser Gly Lys Ser Ala Val Gln Gly
145                 150                 155                 160
```

```
Pro Pro Glu Arg Asp Leu Cys Gly Cys Tyr Ser Val Ser Ser Val Leu
            165                 170                 175

Pro Gly Cys Ala Gln Pro Trp Asn His Gly Glu Thr Phe Thr Cys Thr
        180                 185                 190

Ala Ala His Pro Glu Leu Lys Thr Pro Leu Thr Ala Asn Ile Thr Lys
        195                 200                 205

Ser Gly Asn Thr Phe Arg Pro Glu Val His Leu Leu Pro Pro Pro Ser
    210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
            260                 265                 270

Ser Gln Gly Thr Thr Thr Phe Ala Val Thr Ser Ile Leu Arg Val Ala
        275                 280                 285

Ala Glu Asp Trp Lys Lys Gly Asp Thr Phe Ser Cys Met Val Gly His
        290                 295                 300

Glu Ala Leu Pro Leu Ala Phe Thr Gln Lys Thr Ile Asp Arg Met Ala
305                 310                 315                 320

Gly Lys Pro Thr His Val Asn Val Ser Val Val Met Ala Glu Val Asp
                325                 330                 335

Gly Thr Cys Tyr
            340

<210> SEQ ID NO 79
<211> LENGTH: 344
<212> TYPE: PRT
<213> ORGANISM: Mus musculus

<400> SEQUENCE: 79

Glu Ser Ala Arg Asn Pro Thr Ile Tyr Pro Leu Thr Leu Pro Pro Ala
1               5                   10                  15

Leu Ser Ser Asp Pro Val Ile Ile Gly Cys Leu Ile His Asp Tyr Phe
            20                  25                  30

Pro Ser Gly Thr Met Asn Val Thr Trp Gly Lys Ser Gly Lys Asp Ile
        35                  40                  45

Thr Thr Val Asn Phe Pro Pro Ala Leu Ala Ser Gly Gly Arg Tyr Thr
    50                  55                  60

Met Ser Asn Gln Leu Thr Leu Pro Ala Val Glu Cys Pro Glu Gly Glu
65                  70                  75                  80

Ser Val Lys Cys Ser Val Gln His Asp Ser Asn Pro Val Gln Glu Leu
                85                  90                  95

Asp Val Asn Cys Ser Gly Pro Thr Pro Pro Pro Ile Thr Ile Pro
            100                 105                 110

Ser Cys Gln Pro Ser Leu Ser Leu Gln Arg Pro Ala Leu Glu Asp Leu
        115                 120                 125

Leu Leu Gly Ser Asp Ala Ser Ile Thr Cys Thr Leu Asn Gly Leu Arg
    130                 135                 140

Asn Pro Glu Gly Ala Val Phe Thr Trp Glu Pro Ser Thr Gly Lys Asp
145                 150                 155                 160

Ala Val Gln Lys Lys Ala Val Gln Asn Ser Cys Gly Cys Tyr Ser Val
                165                 170                 175

Ser Ser Val Leu Pro Gly Cys Ala Glu Arg Trp Asn Ser Gly Ala Ser
            180                 185                 190
```

```
Phe Lys Cys Thr Val Thr His Pro Glu Ser Gly Thr Leu Thr Gly Thr
            195                 200                 205

Ile Ala Lys Val Thr Val Asn Thr Phe Pro Pro Gln Val His Leu Leu
        210                 215                 220

Pro Pro Pro Ser Glu Glu Leu Ala Leu Asn Glu Leu Leu Ser Leu Thr
225                 230                 235                 240

Cys Leu Val Arg Ala Phe Asn Pro Lys Glu Val Leu Val Arg Trp Leu
                245                 250                 255

His Gly Asn Glu Glu Leu Ser Pro Glu Ser Tyr Leu Val Phe Glu Pro
            260                 265                 270

Leu Lys Glu Pro Gly Glu Gly Ala Thr Thr Tyr Leu Val Thr Ser Val
        275                 280                 285

Leu Arg Val Ser Ala Glu Thr Trp Lys Gln Gly Asp Gln Tyr Ser Cys
    290                 295                 300

Met Val Gly His Glu Ala Leu Pro Met Asn Phe Thr Gln Lys Thr Ile
305                 310                 315                 320

Asp Arg Leu Ser Gly Lys Pro Thr Asn Val Ser Val Ser Val Ile Met
                325                 330                 335

Ser Glu Gly Asp Gly Ile Cys Tyr
            340

<210> SEQ ID NO 80
<211> LENGTH: 299
<212> TYPE: PRT
<213> ORGANISM: Oryctolagus cuniculus

<400> SEQUENCE: 80

Gln Ser Gly Thr Ser Gly Pro Tyr Thr Ala Cys Ser Glu Leu Ile Leu
1               5                   10                  15

Pro Val Thr Gln Cys Leu Gly Gln Lys Ser Ala Ala Cys His Val Glu
            20                  25                  30

Tyr Asn Ser Val Ile Asn Glu Ser Leu Pro Val Pro Phe Pro Asp Cys
        35                  40                  45

Cys Pro Ala Asn Ser Cys Cys Thr Cys Pro Ser Ser Ser Ser Arg Asn
    50                  55                  60

Leu Ile Ser Gly Cys Gln Pro Ser Leu Ser Leu Gln Arg Pro Asp Leu
65                  70                  75                  80

Gly Asp Leu Leu Leu Gly Arg Asp Ala Ser Leu Thr Cys Thr Leu Ser
                85                  90                  95

Gly Leu Lys Asn Pro Glu Asp Ala Val Phe Thr Trp Glu Pro Thr Asn
            100                 105                 110

Gly Asn Glu Pro Val Gln Gln Arg Ala Gln Arg Asp Leu Ser Gly Cys
        115                 120                 125

Tyr Ser Val Ser Ser Val Leu Pro Ser Ser Ala Glu Thr Trp Lys Ala
    130                 135                 140

Arg Thr Glu Phe Thr Cys Thr Val Thr His Pro Glu Ile Asp Ser Gly
145                 150                 155                 160

Ser Leu Thr Ala Thr Ile Ser Arg Gly Val Val Thr Pro Pro Gln Val
                165                 170                 175

His Leu Leu Pro Pro Pro Ser Glu Glu Leu Ala Leu Asn Glu Gln Val
            180                 185                 190

Thr Leu Thr Cys Leu Val Arg Gly Phe Ser Pro Lys Asp Val Leu Val
        195                 200                 205

Ser Trp Arg His Gln Gly Gln Glu Val Pro Glu Asp Ser Phe Leu Val
```

```
                  210                 215                 220
Trp Lys Ser Met Pro Glu Ser Ser Gln Asp Lys Ala Thr Tyr Ala Ile
225                 230                 235                 240

Thr Ser Leu Leu Arg Val Pro Ala Glu Asp Trp Asn Gln Gly Asp Thr
                    245                 250                 255

Tyr Ser Cys Met Val Gly His Glu Gly Leu Ala Glu His Phe Thr Gln
                260                 265                 270

Lys Thr Ile Asp Arg Leu Ala Gly Lys Pro Thr His Val Asn Val Ser
            275                 280                 285

Val Val Val Ala Asp Val Glu Ala Val Cys Tyr
            290                 295

<210> SEQ ID NO 81
<211> LENGTH: 353
<212> TYPE: PRT
<213> ORGANISM: Gorilla gorilla

<400> SEQUENCE: 81

Ala Ser Pro Thr Ser Pro Lys Val Phe Pro Leu Ser Leu Cys Ser Thr
1               5                   10                  15

Gln Pro Asp Gly Asp Val Val Ala Cys Leu Val Gln Gly Phe Phe
                20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Pro Asp Gly
65                  70                  75                  80

Lys Ser Val Thr Cys His Val Asn His Tyr Thr Asn Pro Ser Gln Asp
                85                  90                  95

Val Thr Val Pro Cys Arg Val Pro Ser Thr Pro Pro Thr Pro Ser Pro
            100                 105                 110

Ser Thr Pro Pro Thr Pro Ser Pro Pro Cys Cys His Pro Arg Leu Ser
        115                 120                 125

Leu His Arg Pro Ala Leu Glu Asp Leu Leu Leu Gly Ser Glu Ala Asn
    130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Glu Gly Pro Pro Glu
                165                 170                 175

Arg Asp Leu Cys Gly Cys Tyr Ser Val Ser Ser Val Leu Pro Gly Cys
            180                 185                 190

Ala Glu Pro Trp Asn His Gly Lys Thr Phe Thr Cys Thr Ala Ala Tyr
        195                 200                 205

Pro Glu Ser Lys Thr Pro Leu Thr Ala Thr Leu Ser Lys Ser Gly Asn
    210                 215                 220

Met Phe Arg Pro Glu Val His Leu Leu Pro Pro Ser Glu Glu Leu
225                 230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
        275                 280                 285
```

Thr Thr Thr Phe Ala Val Thr Ser Ile Leu Arg Val Ala Ala Glu Asp
290                     295                     300

Trp Lys Lys Gly Asp Thr Phe Ser Cys Met Val Gly His Glu Ala Leu
305                     310                     315                     320

Pro Leu Ala Phe Thr Gln Lys Thr Ile Asp Arg Leu Ala Gly Lys Pro
                325                     330                     335

Thr His Val Asn Val Ser Val Val Met Ala Glu Val Asp Gly Thr Cys
                340                     345                     350

Tyr

<210> SEQ ID NO 82
<211> LENGTH: 337
<212> TYPE: PRT
<213> ORGANISM: Sus scrofa

<400> SEQUENCE: 82

Ser Glu Thr Ser Pro Lys Ile Phe Pro Leu Thr Leu Gly Ser Ser Glu
1               5                       10                      15

Pro Ala Gly Tyr Val Val Ile Ala Cys Leu Val Arg Asp Phe Phe Pro
                20                      25                      30

Ser Glu Pro Leu Thr Val Thr Trp Ser Pro Ser Arg Glu Gly Val Ile
            35                      40                      45

Val Arg Asn Phe Pro Pro Ala Gln Ala Gly Gly Leu Tyr Thr Met Ser
50                      55                      60

Ser Gln Leu Thr Leu Pro Val Glu Gln Cys Pro Ala Asp Gln Ile Leu
65                      70                      75                      80

Lys Cys Gln Val Gln His Leu Ser Lys Ser Ser Gln Ser Val Asn Val
                85                      90                      95

Pro Cys Lys Asp Pro Cys Pro Gln Cys Cys Lys Pro Ser Leu Ser Leu
            100                     105                     110

Gln Pro Pro Ala Leu Ala Asp Leu Leu Leu Gly Ser Asn Ala Ser Leu
        115                     120                     125

Thr Cys Thr Leu Ser Gly Leu Lys Lys Ser Glu Gly Val Ser Phe Thr
130                     135                     140

Trp Gln Pro Ser Gly Gly Lys Asp Ala Val Gln Ala Ser Pro Thr Arg
145                     150                     155                     160

Asp Ser Cys Gly Cys Tyr Ser Val Ser Ser Ile Leu Pro Gly Cys Ala
                165                     170                     175

Asp Pro Trp Asn Lys Gly Glu Thr Phe Ser Cys Thr Ala Ala His Ser
            180                     185                     190

Glu Leu Lys Ser Ala Leu Thr Ala Thr Ile Thr Lys Pro Lys Val Asn
        195                     200                     205

Thr Phe Arg Pro Gln Val His Leu Leu Pro Pro Ser Glu Glu Leu
210                     215                     220

Ala Leu Asn Glu Leu Val Thr Leu Thr Cys Leu Val Arg Gly Phe Ser
225                     230                     235                     240

Pro Lys Asp Val Leu Val Arg Trp Leu Gln Gly Gln Glu Leu Pro
                245                     250                     255

Arg Asp Lys Tyr Leu Val Trp Glu Ser Leu Pro Glu Pro Gly Gln Ala
            260                     265                     270

Ile Pro Thr Tyr Ala Val Thr Ser Val Leu Arg Val Asp Ala Glu Asp
        275                     280                     285

Trp Lys Gln Gly Asp Thr Phe Ser Cys Met Val Gly His Glu Ala Leu
290                     295                     300

```
Pro Leu Ala Phe Thr Gln Lys Thr Ile Asp Arg Leu Ala Gly Lys Pro
305                 310                 315                 320

Thr His Val Asn Val Ser Val Val Met Ala Glu Ala Glu Gly Ile Cys
                325                 330                 335

Tyr
```